(12) United States Patent
Ueltschi et al.

(10) Patent No.: US 11,227,509 B2
(45) Date of Patent: Jan. 18, 2022

(54) SURGICAL SIMULATOR SYSTEMS AND METHODS

(71) Applicant: Help Me See Inc., New York, NY (US)

(72) Inventors: Albert Lee Ueltschi, (Deceased), OK (US); Dennis Gulasy, Tulsa, OK (US); Glenn Strauss, Tyler, TX (US); James Tyler Ueltschi, Vero Beach, FL (US); Saro Jahani, Green Brook, NJ (US)

(73) Assignee: Help Me See Inc., New York, NY (US)

( * ) Notice: Subject to any disclaimer, the term of this patent is extended or adjusted under 35 U.S.C. 154(b) by 0 days.

(21) Appl. No.: 16/564,110

(22) Filed: Sep. 9, 2019

(65) Prior Publication Data

US 2020/0005677 A1  Jan. 2, 2020

Related U.S. Application Data

(63) Continuation-in-part of application No. 14/983,037, filed on Dec. 29, 2015, now abandoned.

(60) Provisional application No. 62/097,504, filed on Dec. 29, 2014.

(51) Int. Cl.
   *G09B 23/30*   (2006.01)
   *G09B 23/28*   (2006.01)
   *A61F 9/007*   (2006.01)

(52) U.S. Cl.
   CPC ........ *G09B 23/285* (2013.01); *A61F 9/00736* (2013.01); *G09B 23/30* (2013.01)

(58) Field of Classification Search
   CPC ...... G09B 23/28; G09B 34/10; G09B 23/281; G09B 23/283; G09B 23/285; A61B 34/10; A61B 2034/105

USPC .......................................................... 434/262
   See application file for complete search history.

(56) References Cited

U.S. PATENT DOCUMENTS

| | | | |
|---|---|---|---|
| 5,766,016 A * | 6/1998 | Sinclair .................. | G09B 23/28 434/262 |
| 5,843,070 A | 12/1998 | Cambier et al. | |
| 7,121,832 B2 | 10/2006 | Hsieh et al. | |
| 7,291,016 B2 | 11/2007 | Otto | |
| 7,812,815 B2 | 10/2010 | Banerjee et al. | |
| 7,850,456 B2 | 12/2010 | Chosack et al. | |
| | (Continued) | | |

OTHER PUBLICATIONS

Georgia Institute of Technology, Interactive Media Technology, "Eye Surgery Simulator," www.imtcdrupal.mtc.gatech.edu/content/eye-surgery-simulator.

(Continued)

*Primary Examiner* — James B Hull
(74) *Attorney, Agent, or Firm* — Kelley Drye & Warren LLP

(57) ABSTRACT

A surgical simulator comprising a haptic arm capable of simulating forces generated during surgery from interactions between a surgical tool and tissue operated upon. The simulator further comprises a visual display capable of depicting a three-dimensional image of the simulated surgical tool and a physics-based computer model of the tissue. The haptic arm controls the movement and orientation of the simulated tool in the three-dimensional image, and provides haptic feedback forces to simulate forces experienced during surgery. Methods for simulating surgery and training users of the simulator are also described.

20 Claims, 20 Drawing Sheets

(56) References Cited

U.S. PATENT DOCUMENTS

| | | | |
|---|---|---|---|
| 7,866,983 B2 | 1/2011 | Hemphill et al. | |
| 7,896,653 B2 | 3/2011 | Nylen | |
| 8,311,791 B1 | 11/2012 | Avisar | |
| 8,500,451 B2 | 8/2013 | Bronstein et al. | |
| 8,647,125 B2 | 2/2014 | Johns et al. | |
| 8,650,005 B2 | 2/2014 | Liao | |
| 8,651,858 B2 | 2/2014 | Berckmans, III et al. | |
| 8,662,900 B2 | 3/2014 | Bell, III et al. | |
| 8,682,062 B2 | 3/2014 | Kim et al. | |
| 8,690,581 B2 | 4/2014 | Ruf et al. | |
| 8,794,977 B2 | 8/2014 | McGuan et al. | |
| 8,831,924 B2 | 9/2014 | Avisar | |
| 8,915,743 B2 | 12/2014 | Meglan | |
| 8,924,334 B2 | 12/2014 | Lacey et al. | |
| 2004/0111183 A1 | 6/2004 | Sutherland et al. | |
| 2004/0243147 A1 | 12/2004 | Lipow | |
| 2005/0159759 A1* | 7/2005 | Harbaugh | A61B 34/20 606/130 |
| 2009/0073164 A1 | 3/2009 | Wells | |
| 2010/0195867 A1 | 8/2010 | Kipman | |
| 2010/0249506 A1* | 9/2010 | Prisco | A61B 1/00059 600/117 |
| 2011/0092984 A1* | 4/2011 | Tripathi | A61B 34/20 606/130 |
| 2012/0059378 A1 | 3/2012 | Farrell | |
| 2013/0230837 A1 | 9/2013 | Meglan | |
| 2014/0315174 A1 | 10/2014 | Sassani et al. | |
| 2015/0037775 A1 | 2/2015 | Ottensmeyer et al. | |
| 2015/0049081 A1 | 2/2015 | Coffey | |
| 2019/0142518 A1* | 5/2019 | Viscardi | A61B 34/76 606/130 |
| 2019/0167352 A1* | 6/2019 | Mahfouz | A61B 17/1703 |
| 2019/0183580 A1* | 6/2019 | Ralovich | G06T 17/10 |
| 2020/0005676 A1* | 1/2020 | Kubota | G09B 19/24 |
| 2020/0008877 A1* | 1/2020 | Jo | A61B 34/10 |
| 2020/0078103 A1* | 3/2020 | Duindam | A61B 34/20 |
| 2020/0159313 A1* | 5/2020 | Gibby | A61B 90/36 |

OTHER PUBLICATIONS

PCT International Search Report for International Application No. PCT/US15/67919 dated Mar. 21, 2016.

European Patent Office Examination Report for EP Application No. 15203231.4, dated May 15, 2018.

Chinese Patent Office Search Report for CN Application No. 201580001909.1.

Examination Report issue by Indian Patent Office for Indian Patent Application No. 4919/MUM/2015, dated Feb. 19, 2021.

* cited by examiner

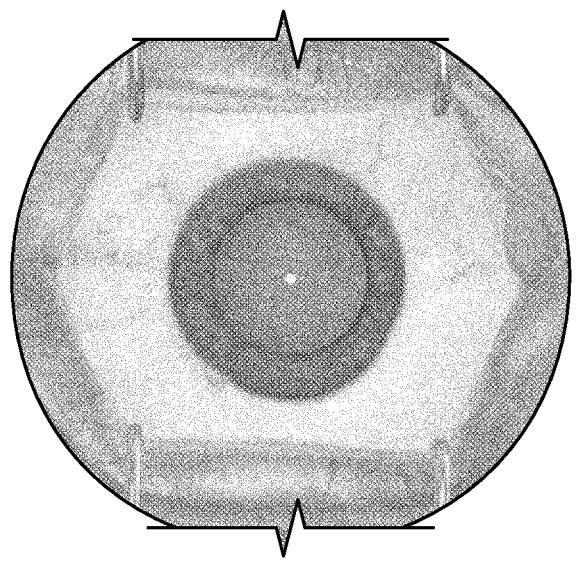 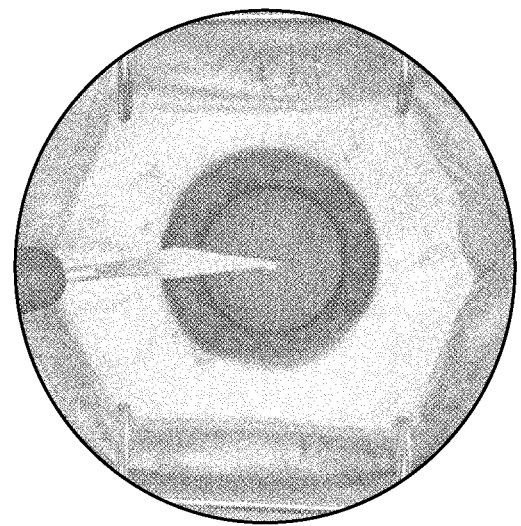
FIG. 5a  FIG. 5b
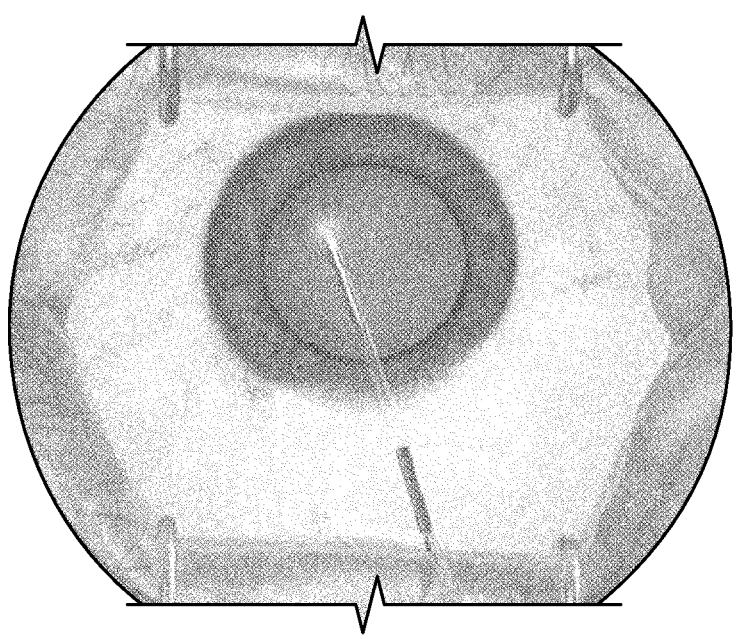
FIG. 5c

Primary haptic device (right hand)

| Handpiece | Simulated instrument | Used in steps |
|---|---|---|
| Round handpiece | Cautery tip | 2 |
| | Crescent blade | 3,4,5,6 |
| | Keratome | 9 |
| | Lens loop | 13,14,15 |
| | Simcoe cannula | 16,17,25 |
| | Sinskey hook | 22,23 |
| | Weck spear | 2,27,30 |
| Syringe handpiece | Viscoelastic syringe, 25g angled cannula | 8,18 |
| | Viscoelastic syringe, cystotome | 10,11 |
| | Saline syringe 25g straight cannula | 12,28 |
| | Saline syringe 25g angled cannula | 24 |
| | Saline syringe 27g angled cannula | 26 |
| | Antibiotic syringe 27g angled cannula | 29 |
| Forceps handpiece | Colibri forceps | 7 |
| | IOL forceps | 19,20,21 |
| Scissors | Scissors | 1* |

FIG. 6a

Secondary haptic device (left hand)

| Handpiece | Simulated instrument | Used in steps |
|---|---|---|
| Round handpiece | 15 degree supersharp | 7 |
| Forceps handpiece | Colibri forceps | 1,2,3,4,5,6,9,13,14,15,19,20,21,27,30 |

FIG. 6b

SURGICAL SIMULATOR SYSTEMS AND METHODS

CROSS-REFERENCE TO RELATED APPLICATIONS

This application is a continuation-in-part of U.S. patent application Ser. No. 14/983,037, filed Dec. 29, 2015, which claims the benefit of U.S. Provisional Patent Application No. 62/097,504, filed on Dec. 29, 2014. The entire contents of these applications are incorporated herein by reference.

FIELD OF THE INVENTION

This invention relates to the field of surgical simulation, and particularly to a surgical simulator system and method of surgery with haptic force feedback.

BACKGROUND OF THE INVENTION

In many parts of the world, people suffer from blindness. Compared to other types of disabilities, the impact of blindness is particularly destructive and can be economically devastating. The blind cannot see to work, to care for themselves, or care for anyone else. In most cases, they do not have access to proper medical care. In most cases, loss of sight from cataracts occurs gradually over many years and results in reduced quality of life, reduced disposable income for the family, and increased reliance on family caretakers (often children who should be in school). General health is impacted as a result of increased risk for injuries, inability to see injuries in order to care for them properly (like cuts and scrapes that can get infected), and reduced ability to maintain proper nutrition. Many of the blind die as a result of their blindness.

In approximately ten years, the number of people afflicted with blindness could double unless something is done. Millions of people with blindness could be cured because blindness is often caused by cataracts that can be removed from the eye to restore sight. Sadly, the resources are simply not available to provide this cure in many parts of the world. In developing nations, resources for the blind are scarce or non-existent, white cane policies (providing awareness and safety for the blind) and other disability legislation are often lacking, and the family carries the burden alone. As a result, cataract blindness is also associated with extreme poverty and increased risk of death.

The fact that cataracts are common also makes blindness an expected disability in developing nations, especially among the poor. It is understood to be part of the aging process and is accepted as such. Information about cataracts and cataract surgery is lacking or incorrect. Patients who have gone to traditional healers or poorly trained surgeons are often given bad information and poor treatment. Surgical treatment is feared and many people would rather stay blind than undergo surgery. As a result, blind patients in developing nations often come to believe that their only choice is to live with blindness, longing to be free of the dark world in which they have been forced to live, but unable to do anything about it.

Phacoemulsification (PE) cataract surgery and conventional extracapsular cataract extraction (ECCE) surgery, with its variants, are the two primary cataract surgery techniques used universally. A popular variant of ECCE surgery that can be performed without sutures is known as manual small incision cataract surgery (MSICS). Although PE cataract surgery is considered the gold standard for cataract removal, it requires expensive machinery and an uninterrupted power source. The overall cost and maintenance of machinery and supplies for PE makes it cost-prohibitive for regions with inadequate infrastructure. PE also has a higher rate of intraoperative complications when it is performed on patients who have advanced cataracts.

MSICS and ECCE are widely practiced outside North America and Europe. A distinct advantage of MSICS over ECCE is that a smaller incision is utilized to remove the cataractous natural lens and implant an intraocular lens (IOL). The smaller incision is also fashioned to be self-sealing and sutureless. This translates into shorter healing times, significantly less astigmatism, reduced intraoperative risk, and overall shorter post-operative recovery. ECCE and MSICS are not dependent on any powered machinery other than an operating microscope. When comparing different surgical techniques and circumstances of application all over the world, MSICS is often the preferred technique for high volume cataract surgery. MSICS can be used to safely and cost effectively restore vision in developing nations where most of the blind live and with the same quality that would be expected in the high tech world. Though there are many variations on the technique, the basic idea of MSICS revolves around properly producing and utilizing a tunnel large enough to deliver even dense cataracts but stable enough to be self-sealing and have minimal impact on the curvature of the cornea.

Even though MSICS is a well proven alternative to address the problem of cataract blindness in developing nations, there is a lack of developing nation eye surgeons skilled in the technique. In some Sub-Saharan African countries for example, there is on average, one ophthalmologist per million individuals. To deal with the burden of global cataract blindness, there is an urgent need to train a substantial number of surgeons in the technique of MSICS. Global cataract blindness rates can be successfully decreased by increasing the number and skill level of available surgeons. A significant part of this training need can be met by high-quality, high efficiency simulation-based training with no patient risk.

There is therefore a need for a surgical simulator system and method that allows the user to master manual small incision cataract surgery or MSICS.

SUMMARY OF THE INVENTION

An object of the present invention is to provide surgical simulator systems and methods that provide visual, haptic, and audio cues to a user to simulate an MSIC surgery.

A further object of the present invention is to provide simulation systems and methods that model tissue, use of surgical tools, and interactions between the surgical tools and the modeled tissue, and allow a user to practice and become proficient in a surgical procedure.

Another object of the present invention is to provide simulation systems and methods that gradually introduce a comprehensive array of realistic patient factors and surgical complications so that the trainee experiences the live feel of surgery, including the many variables and errors that can occur.

Yet another object of the present invention is to provide simulation systems and methods that allow a trainee's performance to be monitored and evaluated for feedback, remedial instruction, scoring and progression.

A further object of the present invention is to provide simulation systems and methods that use a mesh model to build and display visuals using rasterization or ray tracing, while a physical model that influences the properties, such as collision detection and tissue deformation, runs in parallel.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

FIGS. 5a to 5c depict simulated images visible through a simulated microscope in accordance with the present invention.

FIG. 6a is a table of exemplary tools that may be simulated by a haptic right arm in accordance with the present invention.

FIG. 6b is a table of exemplary tools that may be simulated by a haptic left arm in accordance with the present invention.

DETAILED DESCRIPTION OF THE INVENTION

Figure 1:
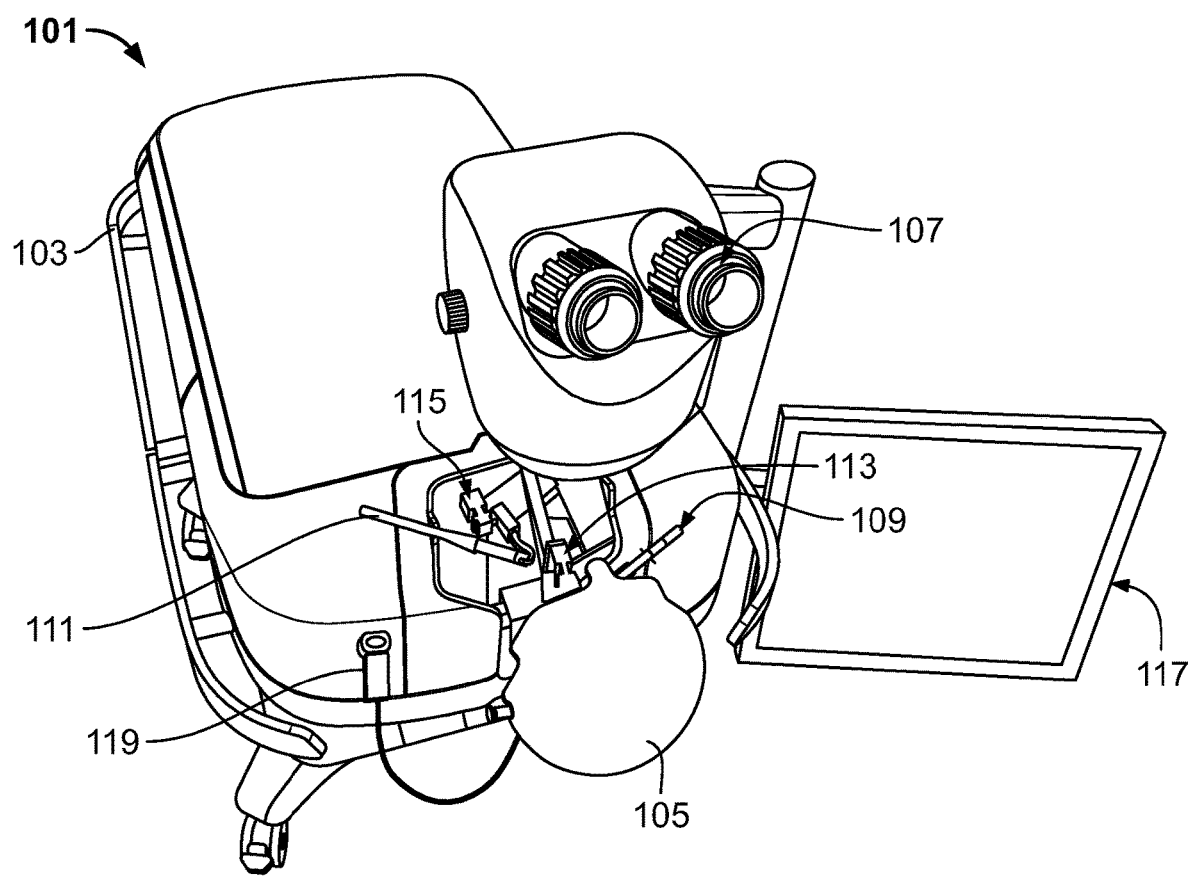
FIG. 1 is a depiction of a simulated surgical environment in accordance with the present invention.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

The present invention is described in the context of MSIC surgery. However, the present invention may be used to simulate other types of surgical procedures performed on the human eye or on other parts of the human body. The present invention may also be used to simulate veterinary surgery. The present invention may also be used to evaluate the skills necessary to perform general surgery or a specific type of surgery when, for example, a medical student is considering whether to pursue a career in surgery, including a career in specialized field of surgery, or at a time shortly before a practicing surgeon performs a surgery.

The present invention may stem the tide of cataract blindness by significantly increasing the number of effective MSICS surgeons in the world. The surgical simulator of the present invention may be used to provide MSICS training on a large scale. The provided training is comprehensive, trainee advancement is based on performance, and successful completion of the training allows the trainee to become part of the global network of cataract surgeons. The training may be administered to persons with no previous knowledge of or experience with eye care. Success in the training program is performance based—each trainees prove that they have the basic language, intellectual, motor skills, and depth perception needed to master MSICS surgery by demonstrating the required performance in order to progress through the training program. Data gathered on admission may be compared with performance during training to refine the admissions testing and establish standardized criteria.

Using the surgical simulator systems and methods of the present invention, the user can progress methodically and efficiently through the learning process, experiencing a spectrum of surgical challenges and variations in a relatively short period of time, without ever endangering a patient. Upon successful completion of the simulator-based training, the trainee may return to surgical facilities in their own country to begin live surgical training under the supervision of a mentoring surgeon. Normally live surgical training may take years to complete and often leaves gaps in the experience. But because of the advanced simulation experience, the users of the present invention can progress rapidly to independent, high quality work. The approximate transition to independent surgical care is expected to take between one to six months.

The surgical simulator and method of the present invention may gradually introduce through simulation a comprehensive array of realistic patient factors and surgical complications associated with each step so that the trainee experiences the live feel of surgery including the many variables, complications, and errors that can occur during a live surgery. Simulator assisted training provides a safe and efficient means to prepare for live surgical experience. The training experience presents a wide variety of surgical situations to develop confidence and surgical intuition for live surgery without risk to patients. Trainee performance on assignments on the simulator may be monitored and evaluated for feedback, remedial instruction, scoring and progression. Each trainee may practice and learn until a desired level of proficiency is demonstrated on the simulator.

For MSICS to be successful, the following five tasks must be completed in sequence during simulation: (1) complete patient preparation, (2) create a self-sealing tunnel into the eye, (3) remove the cataract, (4) insert the intraocular lens ("IOL"), (5) restore conditions that optimize the healing process.

The MSICS simulator comprises the hardware and software to display an eye, both visually and haptically. The simulator provides visual, haptic, and audio cues to the user to simulate a realistic MSIC surgery. The haptic and visual rendering are both preferably derived from live surgical force data, MSICS expert subjective evaluation, and/or objective validation of the models. The haptic rendering may provide the trainee with virtually the same forces on the instruments as experienced during live surgery. The visual rendering may reproduce the images in a non-pixilated stereoscopic display with photorealistic quality, mimicking what a surgeon would see during a live surgery in a binocular operating microscope. The modeling may include: (1) tool-tissue interaction, (2) tissue to tissue interactions, (3) connections between tissues, (4) dissection of tissues, (5) alteration of tissue properties, (6) intraocular pressure, (7) injection and aspiration of fluid, (8) spread of fluid, (9) playing sounds in response to events, and (10) model patient head movement.

The MSICS simulator may consist of the following simulation elements: (a) a simulator with haptic arms, (b) a physics-based computer model, and (c) a visual image generator. The MSICS simulator may also include an instructor/student operator station.

Simulator with Haptic Arms

Figure 2:
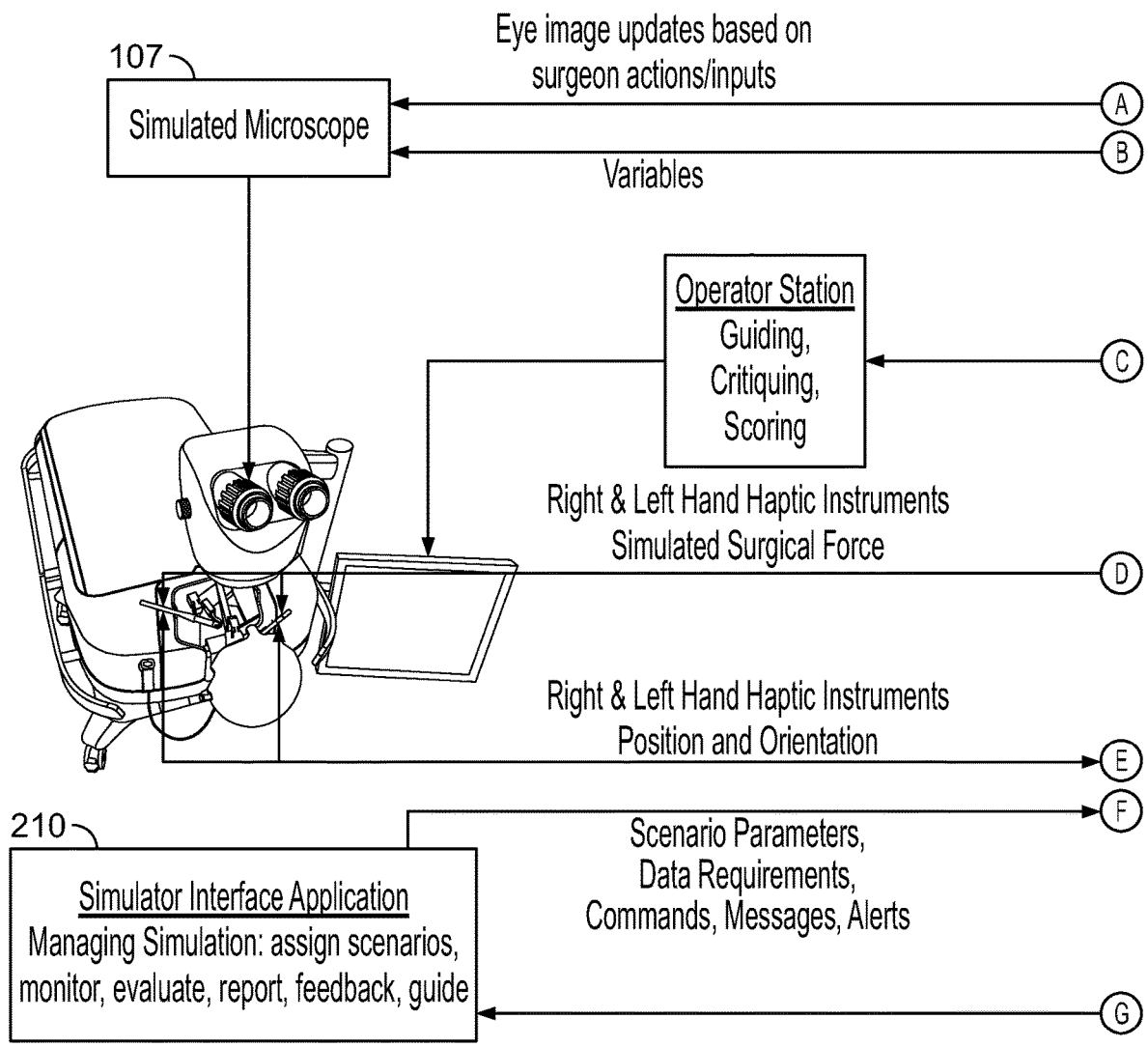
FIG. 2 is a chart depicting the interaction between a simulated surgical environment and computer components in accordance with the present invention.
Figure 2:
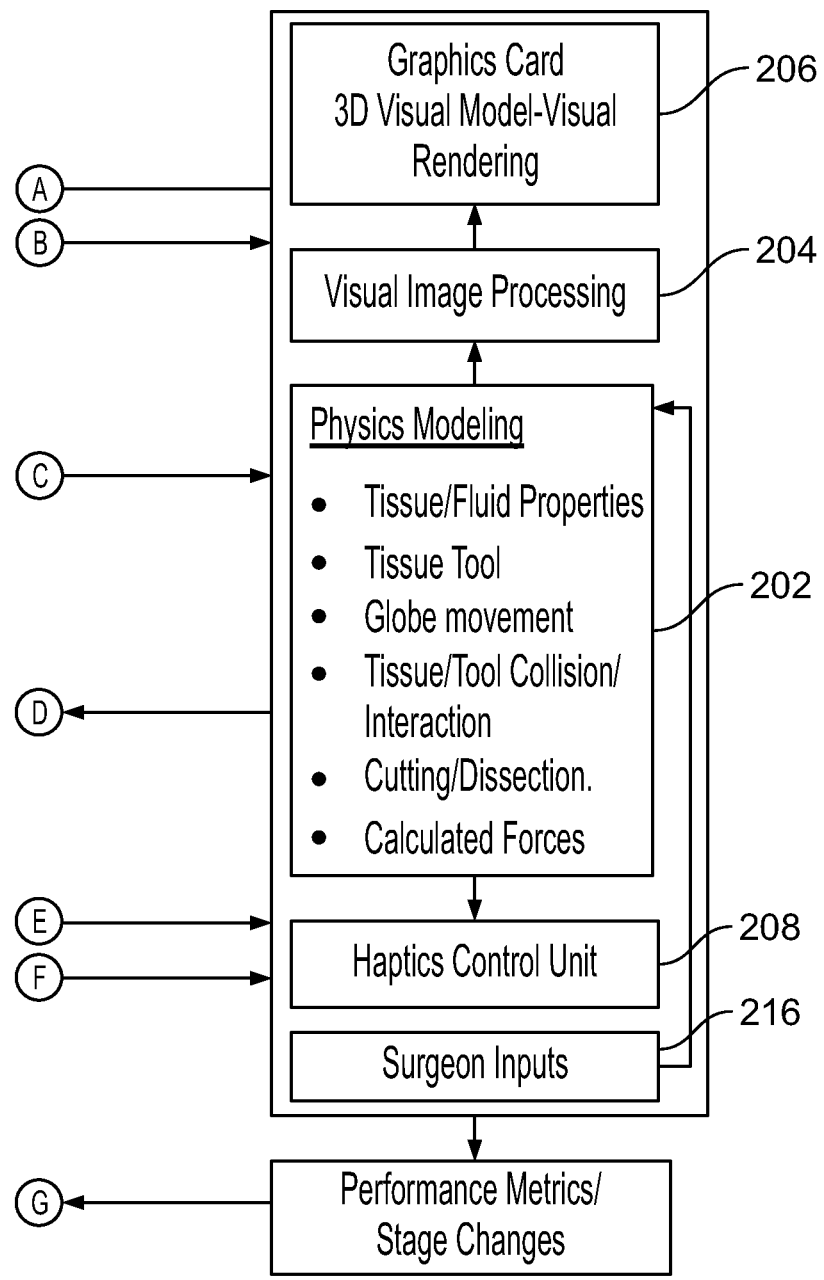

With reference to FIGS. 1 and 2, simulator (101) may comprise gurney body (103) from which a simulated model of a patient's head (105) extends. Simulator (101) may further include simulated microscope (107) through which the user may perceive a simulation. Haptic right arm (109) and haptic left arm (111) may be connected to and controlled by right haptic mechanism (113) and left haptic mechanism (115), respectively. Simulator (101) may further include touch screen (117) and simulated aspiration syringe instrument (119).

A surgeon's hands and fingers are too large to directly manipulate the small and delicate tissues of the eye. As such, to perform MSIC surgery, a surgeon uses certain instruments or tools. In the present invention, those instruments are simulated by haptic right arm (109) and haptic left arm (111). Haptic arms (109, 111) are provided in the workspace and held in a user's right and left hands to simulate the surgery. For example, haptic arms (109, 111) are used to perform actions on a virtual eye while looking through the viewer of microscope (107). A user may select instruments for simulation and move the instruments into the operational area of the simulator under microscope (107). The user can use these instruments to simulate various surgical tasks.

Haptic arms (109, 111) provide tactile realism in the form of force feedback when working on the virtual eye model. Haptic arms (109, 111) are motion control devices that provide a realistic feeling of the forces to the user's fingers, hands and arms holding the instruments as the instruments interact with the virtual eye. The virtual eye is programmed to accurately simulate a response or behavior that would be caused by interactions between an eye and selected instruments. For example, to simulate holding down an eye and increasing pressure in the eye by pressing down on the eye with Colibri forceps, one of the haptic arms (109, 111) may simulate Colibri forceps that may be used to restrict movement of the eye in the viewer of simulated microscope (107). Resistance from the corresponding haptic mechanism (113, 115) may be increased to simulate an increase in hardness of the eye that would be felt by the Colibri forceps or another tool as the tool impinges against the eye. Similarly, simulating interaction with a crescent blade would result in cutting the eye tissues of the virtual eye according to the simulated blade's edge, angle, force, nature of movement etc. The simulator may also simulate interactions between two or more tools.

Haptic arms (109, 111) provide a simultaneous and bimanual use to represent tools used in an actual MSIC surgery. Preferably, haptic arms (109, 111) are representative of actual surgical instruments. In one embodiment, haptic arms (109, 111) allow the changing of handles that are representative of actual surgical instruments. In another embodiment, haptic arms (109, 111) include permanently mounted handles that are representative but may not be exact replicas of actual surgical instruments. In either case, the instrument visual under simulated microscope (107) may change for each type of instrument. The simulator may further simulate other tools, such as, for example, a syringe of the Simcoe Cannula. FIGS. 6a-6b are exemplary lists of tools that may be simulated by the simulator. Each tool may have three translational degrees of freedom. The haptic point of interest for these translations is at the tip of the tool. Three passive rotational degrees of freedom are also provided and measured. Their rotations are centered at this same point of interest. The haptics are based on the use of admittance control, using a force sensor as an input.

As described above, the haptic rendering provides the user with virtually the same forces on the instruments as experienced during live surgery. Table 1 below lists the surgical steps that may be simulated by the simulator, the instrument that may be simulated for each step, a direction of movement of the instrument during surgery, and maximum and minimum values of forces for each surgical step.

TABLE 1

| Surgical step/ Maneuvers | Instrument | Direction Of Movement | Horizontal (Fx gms) | Vertical (Fy gms) | Anterior-posterior (Fz gms) |
|---|---|---|---|---|---|
| Scleral tunnel pocket | Crescent blade | H + AP | Max 48.8 Min 21.7 Avg 31.9 | Max 63.6 Min 35.4 Avg 47.0 | Max 62.5 Min 24.4 Avg 45.6 |
| Scleral tunnel lateral extension | Crescent blade | H | Max 115.8 Min 61.9 Avg 91.3 | Max 87.1 Min 41.0 Avg 60.8 | Max 95.4 Min 43.5 Avg 66.2 |
| Paracentesis port | 15 degree blade | AP | Max Min Avg | Max Min Avg | Max 55.6 Min 13.3 Avg 23.4 |
| AC entry via main incision | Keratome | H + AP | Max 82.2 Min 35.4 Avg 55.6 | Max Min Avg | Max 52.0 Min 2.1 Avg 22.9 |
| Capsulotomy | Cystotome | V | Max Min Avg | Max 42.0 Min 10.9 Avg 22.5 | Max 48.0 Min 13.6 Avg 23.6 |
| Lens expression | Lens vectis | AP | Max Min Avg | Max Min Avg | Max 66.3 Min 7.8 Avg 35.1 |
| IOL repositioning | Sinskey hook | AP + H + V | Max negligible Min Avg | Max negligible Min Avg | Max 7.4 Min 1.6 Avg 4.7 |

In Table 1, all forces are shown in grams (g) and the directions of movements are represented as follows: H—horizontal, AP—antero-posterior, V—vertical. Fx represents the forces in the x plane designating the left-to-right movement, Fy represents the forces in the y plane designating the up-and-down movements, and Fz represents the forces in the z plane designating in-and-out movements. The primary force during the pericentesis stab is Fz inwards, whereas during the "slice" maneuver using the crescent blade, Fx (to the right or left) forces dominate.

Force values set the level of force that the simulator reproduces to give the operator a realistic feel for the procedure. A minimum force establishes the upper limit for noise in the electronics and friction in the robotic mechanism beyond which the surgeon can no longer properly experience the surgical forces. A maximum force sets the standard for the size of the motors and stiffness of the robotic mechanism. The force curve characteristics provide an objective baseline for testing the realism of simulated live tissue interaction.

The most critical step of the MSICS procedure is the creation of the scleral tunnel. It is also the most difficult step to learn. The Fx of the crescent blade during back-and-forth "wiggle" motions when creating the Scleral tunnel pocket averages 31.9 grams with a maximum (max) of 48.8 g and a minimum (min) of 21.7 g. During the same motion, the surgeon is also following the contour of the globe upwards and inwards. The Fy "wiggle" motions of the crescent blade during the Scleral tunnel pocket step (which is an upwards oriented force) is averaged at 47.0 g (max 63.6 g, min 35.4 g). Fz (which is an inwards oriented force) is averaged at 45.6 g (max 62.5 g, min 24.4 g) during this same step. All three degrees of freedom have significant forces during this maneuver. It is important that the surgeon recognize that as the blade wiggles left and right it is also advancing inwards and following the contour of the globe upwards, all up to similar average forces.

The highest force encountered during the simulation is when slicing the crescent blade to the right or left during the Scleral tunnel lateral extension step. Fx of the crescent blade during the "slice" maneuver to the right or left in Scleral tunnel lateral extension step is averaged at 91.3 g (max 115.8 g, min 61.9 g). The MSICS simulator reproduces forces from zero to at least the 115.8 g amount. The y force value for this step changes depending on whether the surgeon is slicing to the right or to the left. When slicing rightwards, Fy is downward in orientation as the left-handed surgeon follows the contour of the globe. When slicing leftwards, the Fy is upward in orientation, as the right-handed surgeon extends the tunnel leftwards while grasping the outer tunnel with Colibri forceps. The z forces encountered are outward in orientation during the crescent slice regardless of the direction of slicing. Fy max when slicing to the right, a downward oriented force, has an average of 31.3 g (max 50.2 g, min 12.0 g). Fy when slicing to the left is an upward oriented force with an average of 60.8 g (max 87.1 g, min 41.0 g). The Fz force (Fz max) during the crescent "slice" maneuver is an outwards oriented force with average of 66.2 g (max 95.4 g, min 43.5 g).

Stab incision forces are predominantly z forces during cornea entry (i.e., or Paracentesis port). Fz during stab incision, or Paracentesis port, formation, using the paracentesis 15 degree blade is inwards in orientation with an average force of 23.4 g (max 55.6 g, min 13.3 g).

Although often taught to "float" in the center of the tunnel slicing the keratome right or left, a novice surgeon would recognize that significant Fx forces can still be encountered, up to an average of 55.6 g, especially toward the far extent of the maneuver. When entering the anterior chamber using the 3.0 mm keratome (i.e., AC entry via main incision), the Fz max (inwards) averages 22.9 g (max 52.0 g, min 2.1 g). The "slicing" with the keratome to open the inner wound, the Fx (right or left) averages 55.6 g (max 82.2 g, min 35.4 g).

The cystotome can-opener forces are provided in the y and z degrees of freedom. There are no significant forces when cutting the anterior capsule during each stroke. The actual cut stroke of the cystotome has minimal forces—a surgeon cannot feel the cystotome cutting the anterior capsule. However, a significant reposition force (Fy upwards and Fz outwards) signature is provided immediately after each cutting stroke. Fy for the Capsulotomy step is an upwards oriented force which averages 22.5 g (max 42.0 g, min 10.9 g) and Fz in an outwards oriented force averages 23.6 g (max 48.0 g, min 13.6 g).

Fz (oriented outwards) during the vectis expression of the crystalline lens averages 35.1 g (max 66.3 g, min 7.8 g). Sinskey forces are minimal when dialing the IOL, highlighting that to properly dial an IOL under viscoelastic control requires minimum forces. Maximum forces in any degree of freedom when dialing the IOL with the Sinskey hook at the 9 o'clock position are negligible, with an average of 4.7 g (max 7.4 g, min 1.6 g).

Physics Based Computer Model

FIG. 2 is a chart illustrating the flow of data between simulator components during a simulation. A physics modeling application (202) models the tissue and fluid properties of the simulated eye and the interaction of the tools with the eye, including the forces applied by tools to the eye. Information concerning the visual appearance of the eye and the tools may be processed by a visual image processing application (204) and delivered to a graphics card (206) for 3-D model rendering. The 3-D image of the eye is transmitted to simulated microscope (107) and may be viewed by a user during a simulation.

Haptics control unit (208) receives simulation modeling information from the physics modeling application. Haptics control unit (208) further receives surgical input information (216) from haptic arms (109, 111) concerning the position and orientation of haptic arms (109, 111). Haptics control unit (208) controls the amount of force and resistance applied by haptic mechanisms (113, 115) to haptic arms (109, 111).

The simulator further includes a simulator interface application (210) that manages the simulation. The simulator interface application (210) allows instructors to assign surgical scenarios to users, and/or monitor, evaluate, provide feedback to and report on users concerning their operation of the simulator.

Figure 3A:
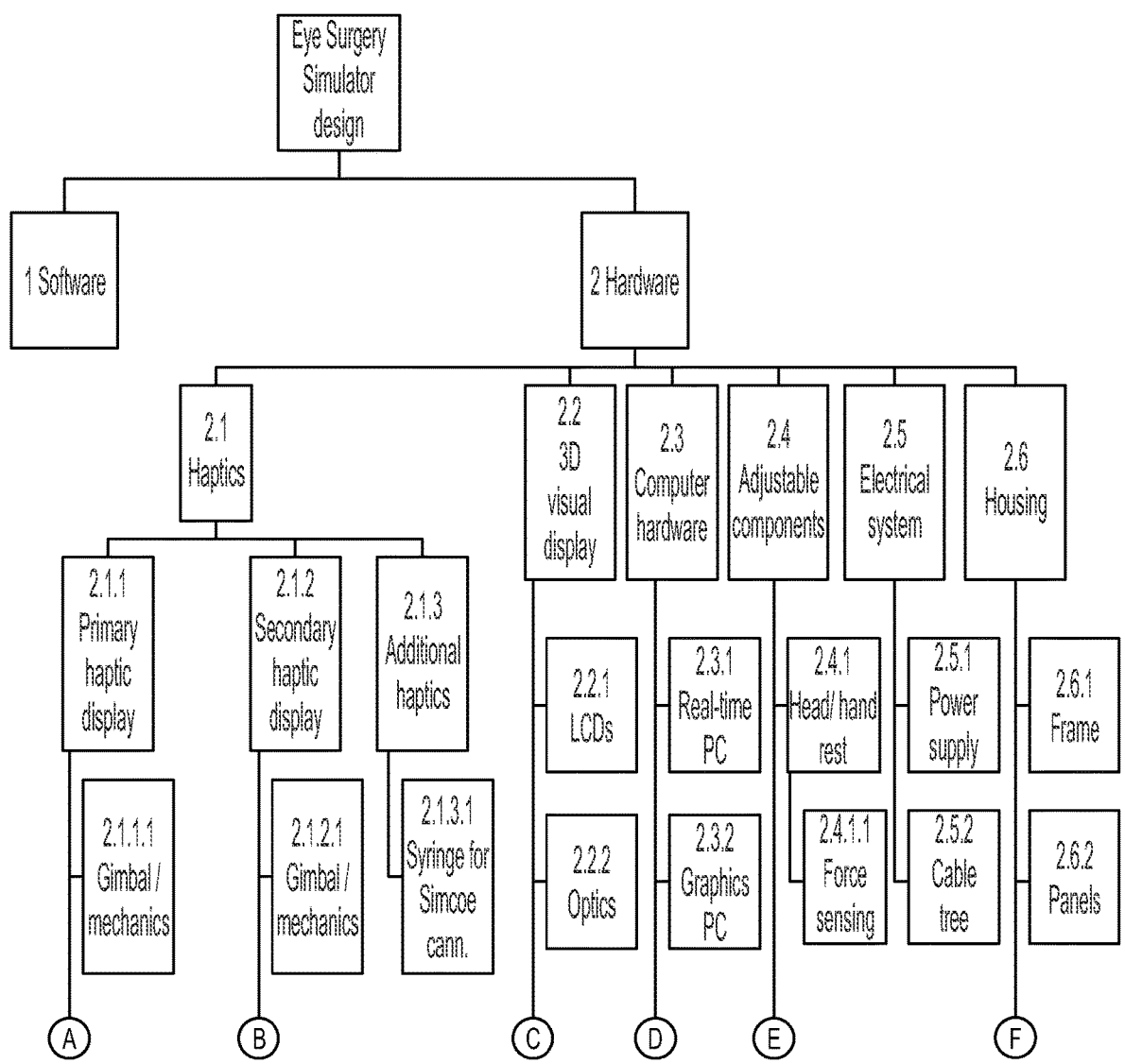
FIG. 3a is a chart illustrating hardware components of a simulator in accordance with the present invention.
Figure 3A:
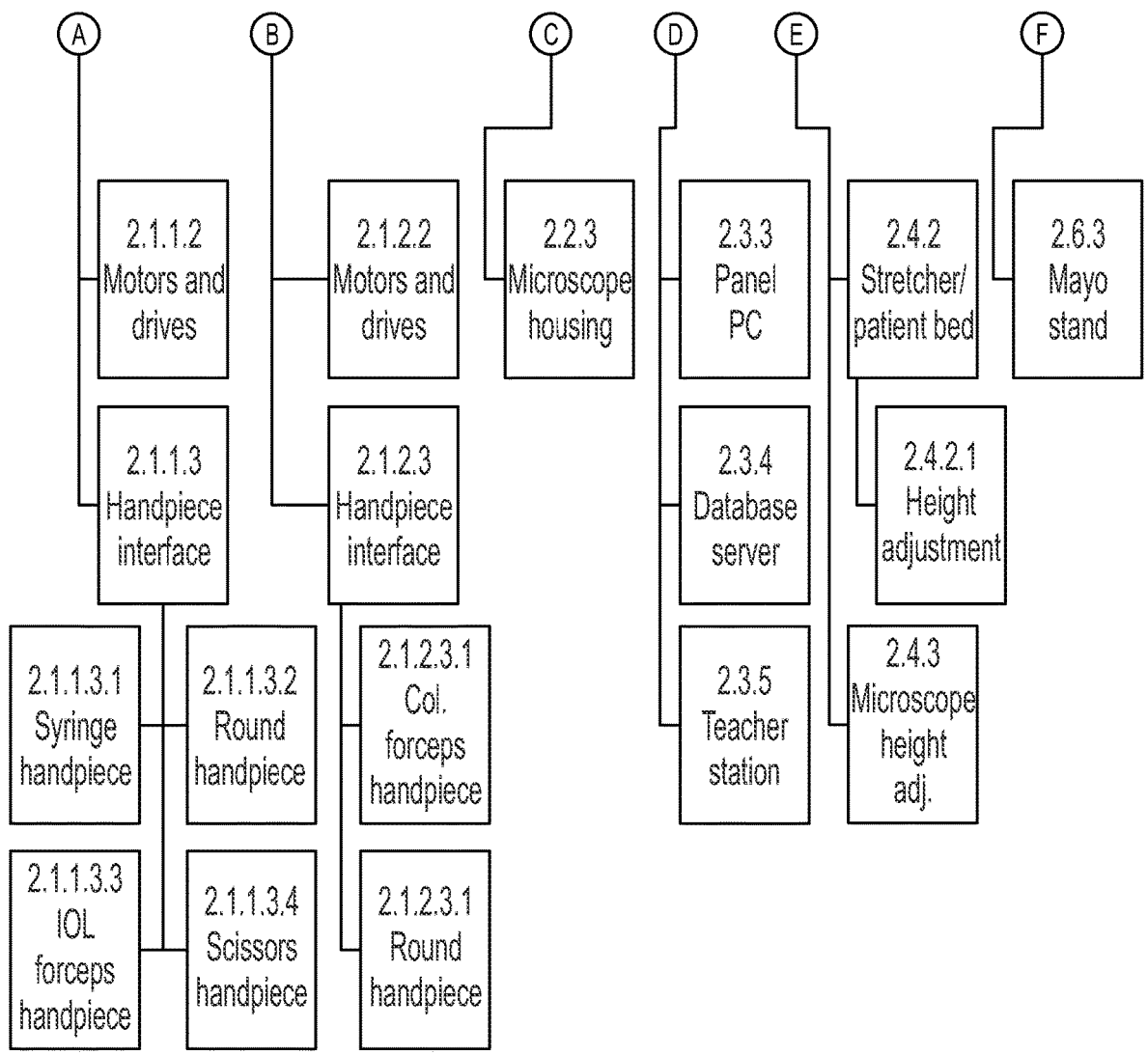

FIG. 3a is a chart illustrating the interrelation of hardware components of the simulator. Haptic components (2.1) may include Gimbal mechanisms (2.1.1.1, 2.1.2.1), motors and drives (2.1.1.2, 2.1.2.2), and hand piece interfaces (2.1.1.3, 2.1.2.3). The 3-D visual display (2.2) of simulated microscope (107) may include one or more LCDs (2.2.1), optics (2.2.2) and a microscope housing (2.2.3). Computer hardware (2.3) used by, sending information to, or receiving information from the simulator may include a real-time PC (2.3.1), a graphics PC (2.3.2), a panel PC (2.3.3), a database server (2.3.4) and/or a teaching station (2.3.5). A simulated head (2.4.1)—depicted in FIG. 1 by reference element (105)—and a stretcher/patient bed (2.4.2)—depicted in FIG. 1 by reference element (103)—may also be provided.

Visual Image Generator

The simulator may represent a visual graphical model of a portion of the body on which surgery may be practiced, such as a graphical model of the eye to simulate a realistic MSIC surgery. A physics based model of the eye may be programmed to simulate the eye behavior in response to surgical actions. The visual 3-D eye model may change according to these actions in real time to give the experience of working with a real eye. The virtual eye may have customizable parameters that allow changing not only the way it appears (e.g., color of the iris, skin, sclera), but also other anatomical and technical parameters, such as its shape and/or, cataract type, to allow a user to practice with a wide range of patient conditions that a surgeon may encounter.

Figure 4A:
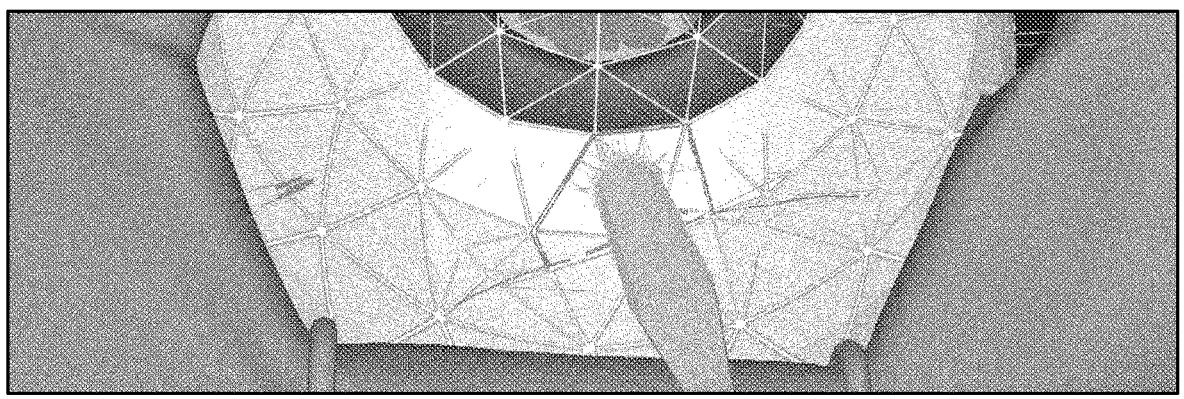
FIGS. 4a to 4f depict simulated physical eye models in accordance with the present invention.
Figure 4B:
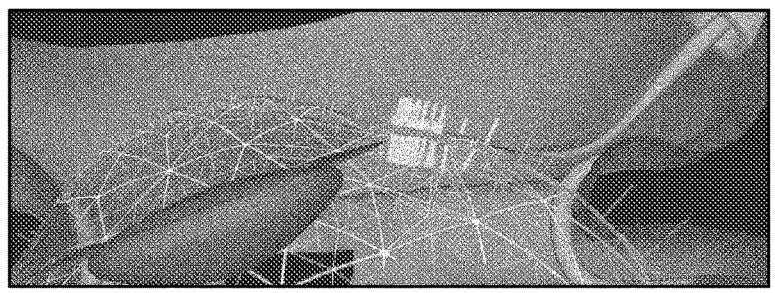
Figure 4C:
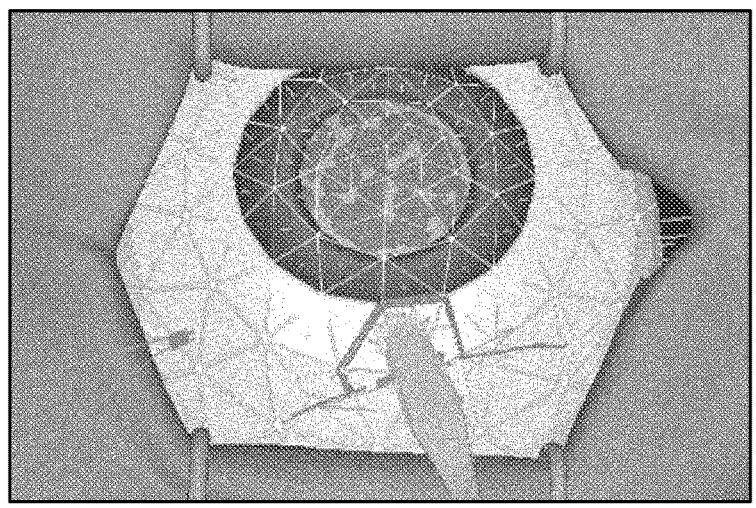
Figure 4D:
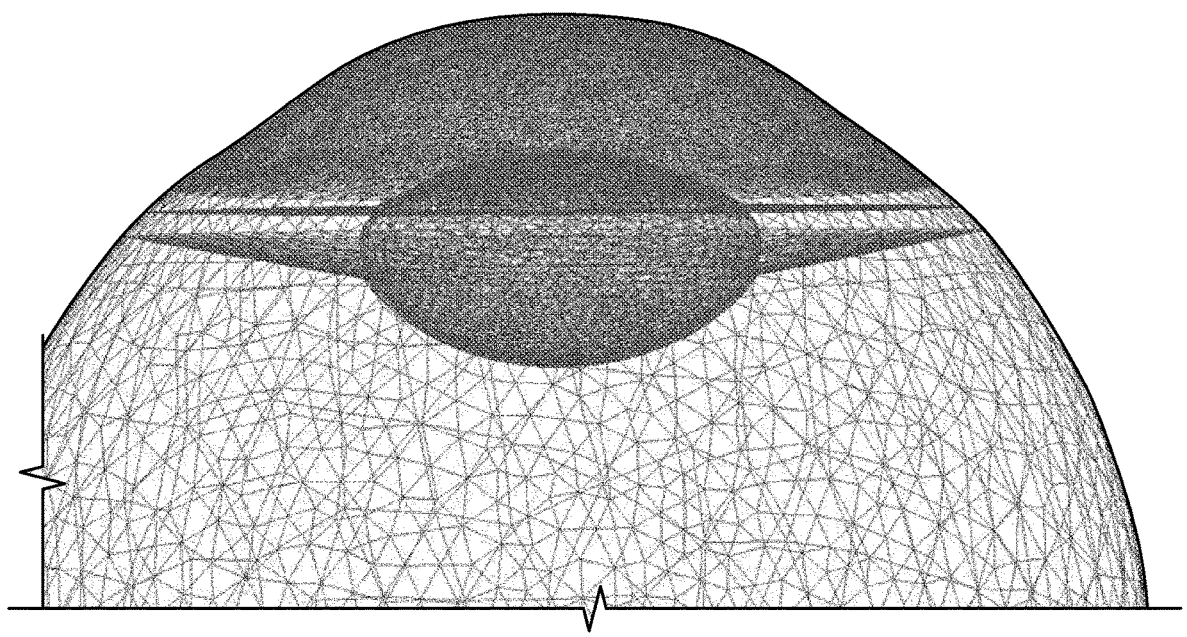
Figure 4E:
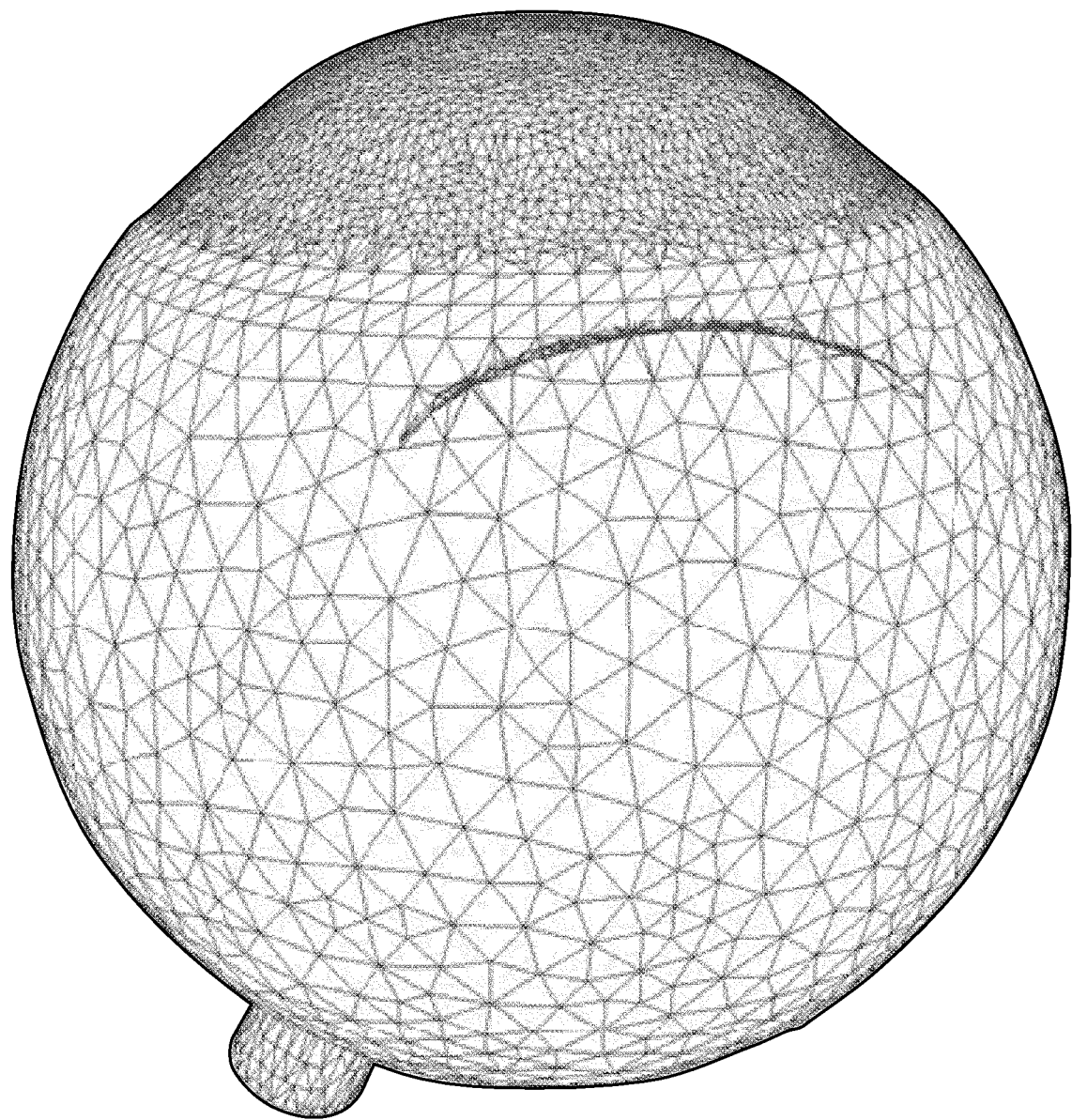
Figure 4F:
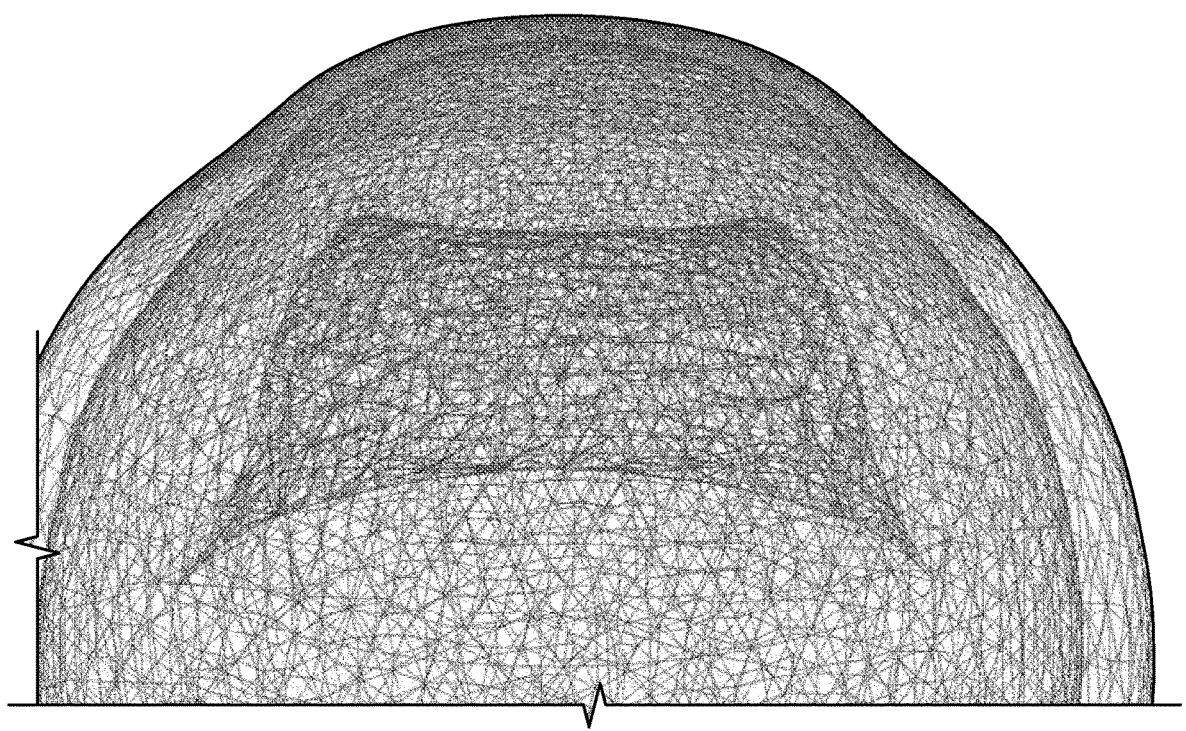
Figure 7A:
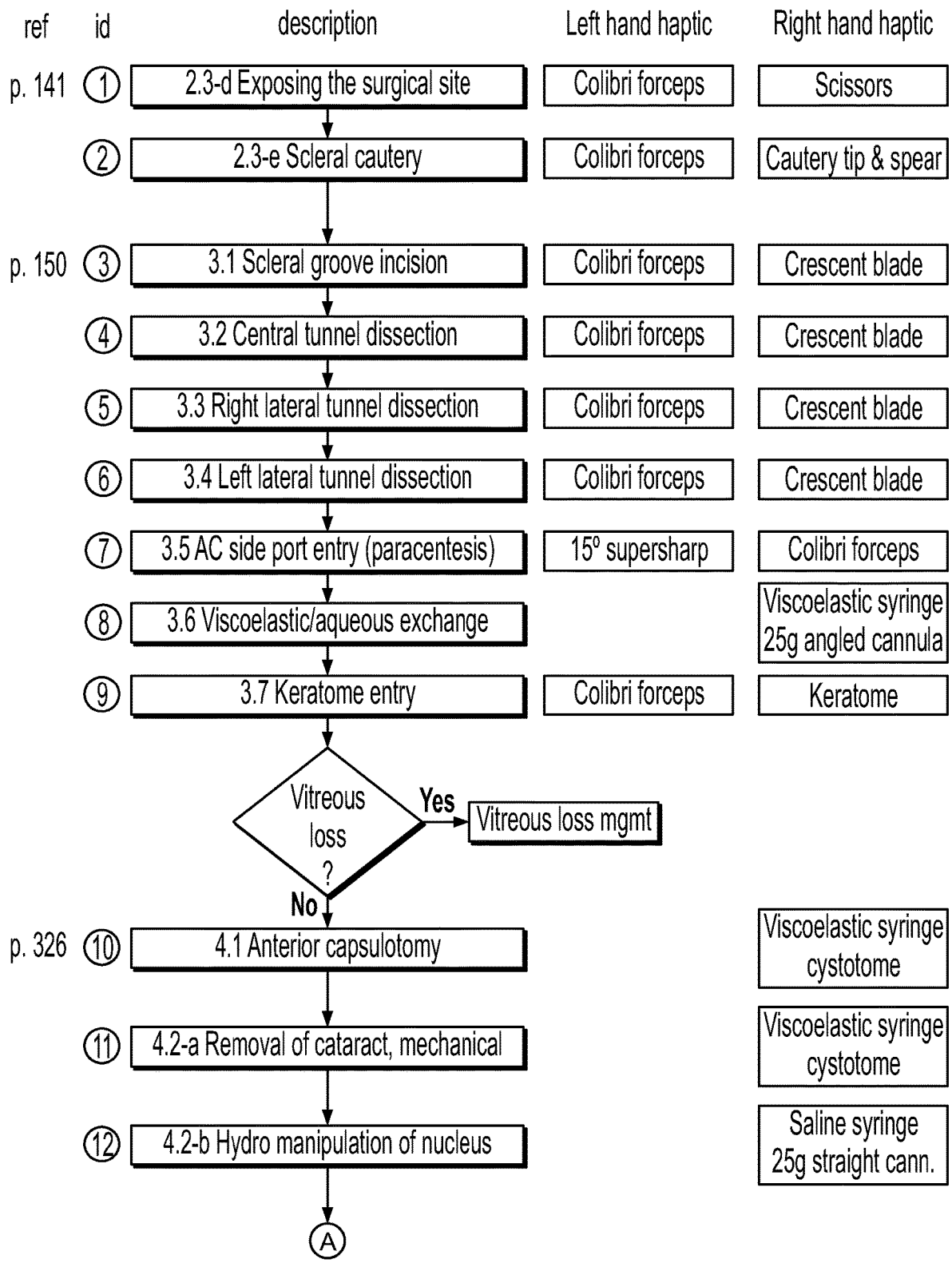
FIGS. 7a and 7b depicts the steps for performing MSIC surgery and the tools that may be simulated by haptic arms in accordance with the present invention.
Figure 7A:
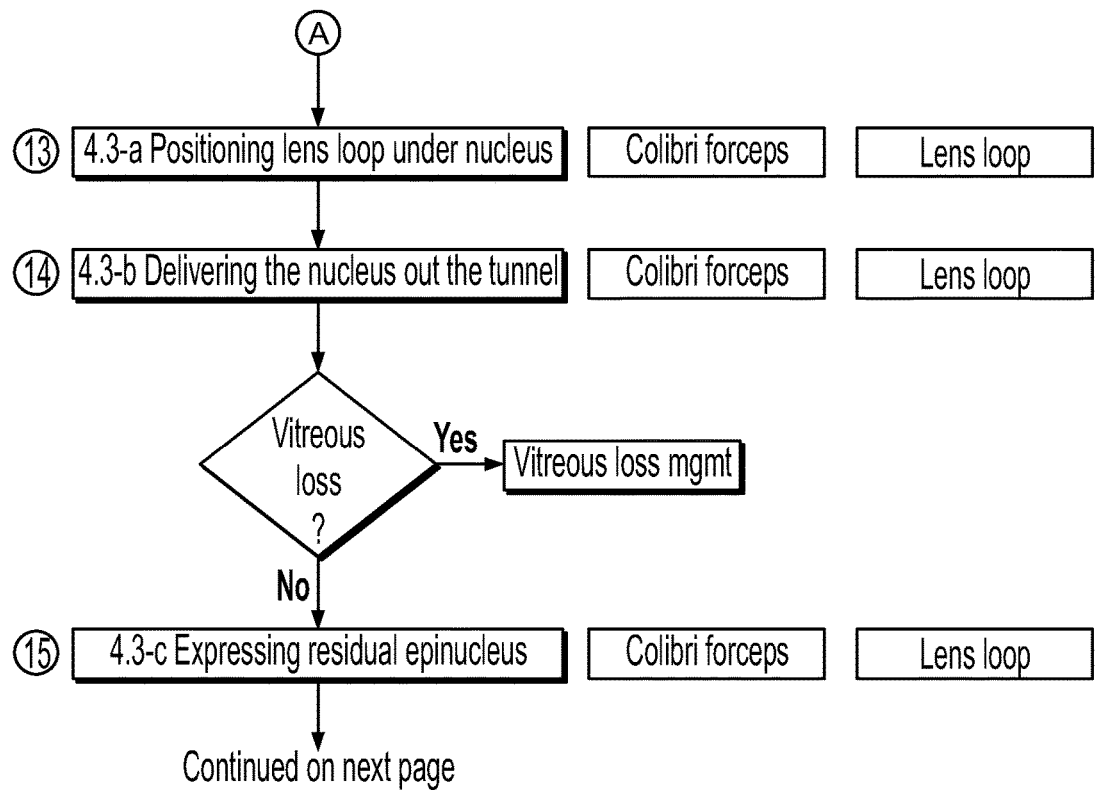
Figure 7B:
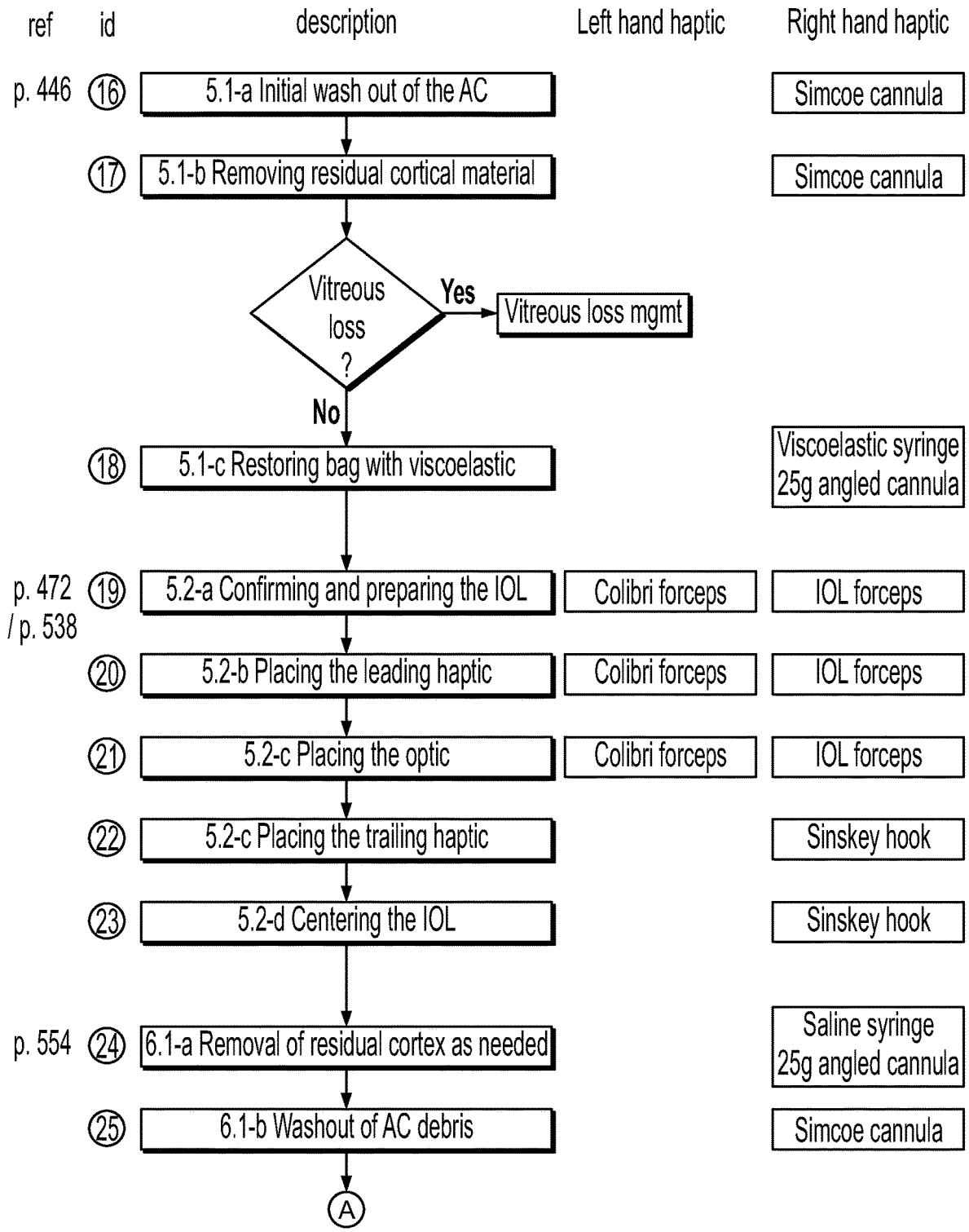
Figure 7B:
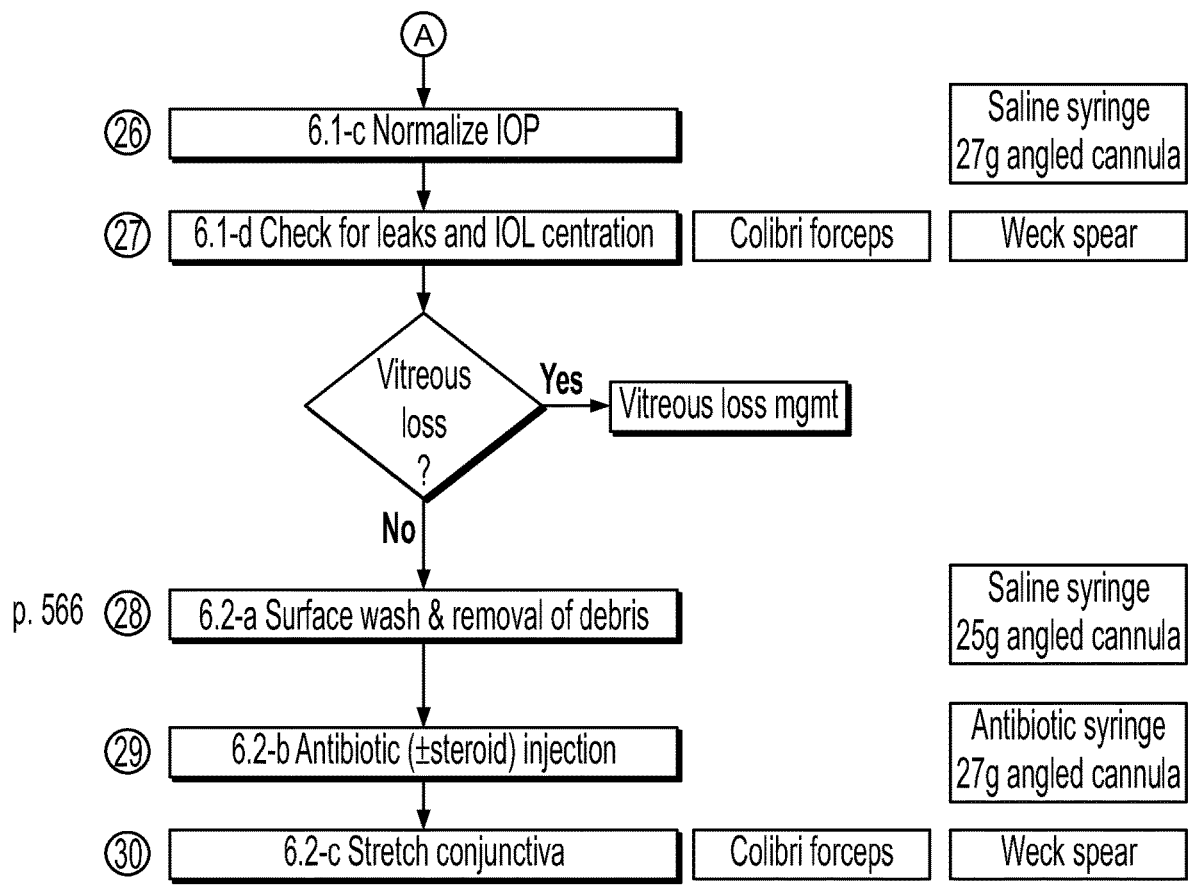

FIGS. 4a-4f illustrate the physics model depiction. As shown in FIGS. 4a-4f, a mesh model may be used to build and display the visuals using rasterization, while a physical model that influences the properties, such as collision detection and tissue deformation, runs in parallel. The eye model may include all the structures involved in the MSICS surgery. The eye model may include high detail for the corneal and limbus to achieve a realistic reflection from its surface. FIG. 4d shows a wireframe rendering of the eye from the side illustrating the high detail may overlap the limbus. FIG. 4e shows the main tunnel as it enters the eye, and FIG. 4f illustrates a wireframe of the main cut.

The simulator may contain two visual displays that a user can work with, including the (1) microscope view, and (2) an external display screen. FIGS. 5a-5c illustrate simulated images within the microscope view. Objects in the simulation are perceived to move and deform with physical realism. The trainee is presented with an image of the visual model through a 3-D visual display that resembles a stereoscopic microscope. Using the microscope, the trainee sees the virtual eye model and interacts with it using the haptic arms (physical forms representing surgical instruments) to perform the tasks while looking through the microscope eyepieces.

The visual display may depict a stereoscopic 3-D image of the eye as would be seen under an operating microscope at 5× magnification showing everything within a surgical field of 34 mm to 35 mm circular area. The image of the field is preferably surrounded by a black ring approximately 5 mm in width, making the total visual image approximately 4 cm in diameter. In a preferred embodiment, rasterization may be used for rendering the visuals for the eye-model. In other embodiments, ray tracing may be used, or a combination of rasterization and ray tracing.

The external display allows the trainee and the instructor to communicate with the simulator. Communications include, but are not limited to the following: selection of the surgical assignment to practice, review the assignment related information on screen before beginning performance, looking at feedback content (multimedia—text, audio, video, animations, etc.), and parallel display of microscope view, for example, when an assignment is being performed, etc. The external display may include a control panel by which the learner and/or instructor exercise control over simulations.

Figure 8:
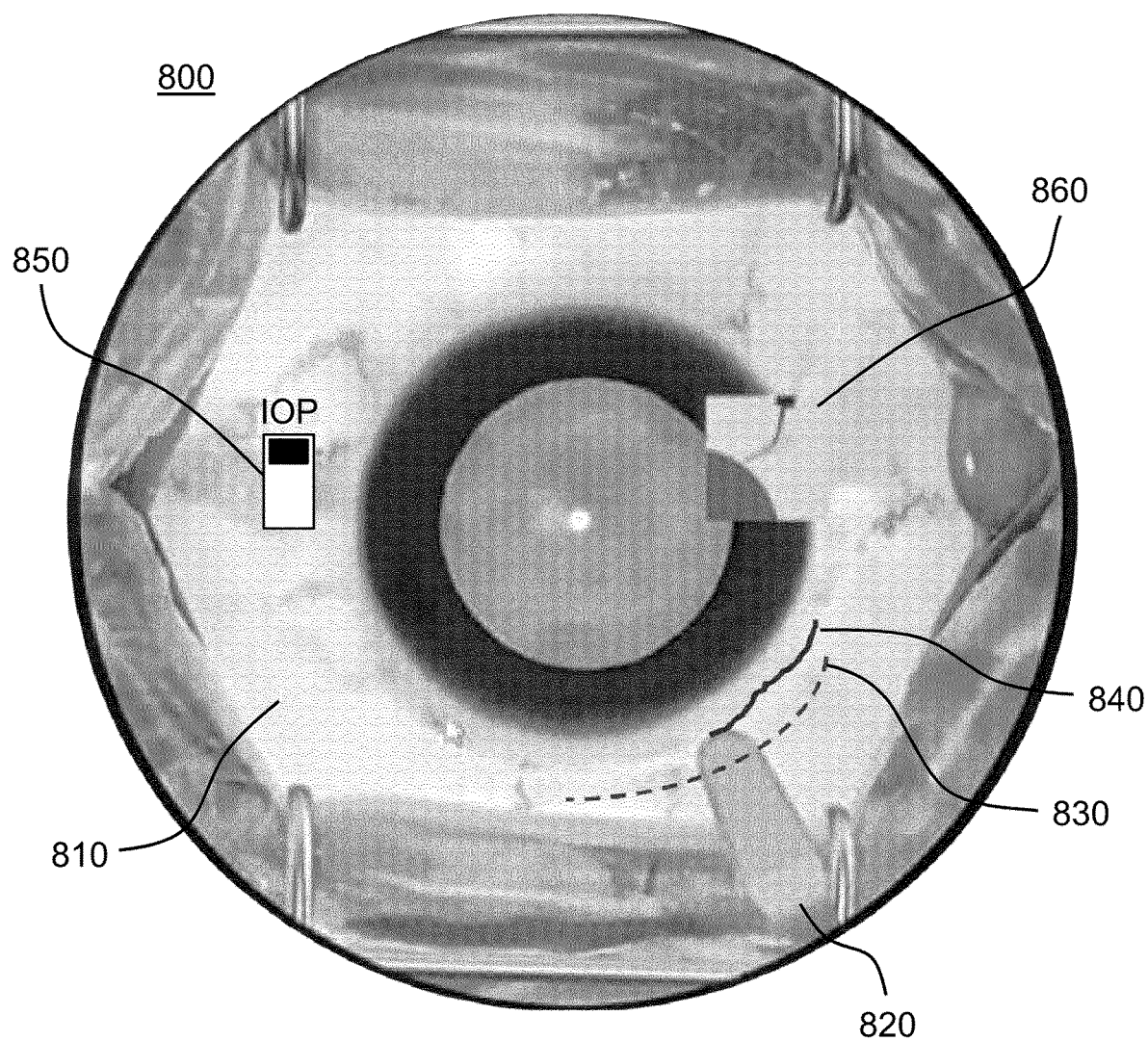
FIG. 8 depicts a simulator user interface in accordance with the present invention.

FIG. 8 depicts an exemplary image (800) within the microscope view in accordance with the present invention. Image (800) may include one or more visual cues and/or information relevant to the simulated procedure that may help guide the trainee and indicate the extent to which the trainee performs the surgical technique with sufficient proficiency. Image (800) may include three-dimensional rendering of an eye (810) and one or more three-dimensional renderings of surgical instruments (820) as controlled by haptic arms (109, 111). Image (800) may include guideline (830) showing the path along which an incision should be made, or the desired path of any instrument. Guideline (830) may be black, white, or a color such as yellow. Guideline (830) may be any type of line, including solid, dotted, or dashed.

Guideline (830) may be displayed while surgical instrument (820) is moved by the user and/or when a portion of surgical instrument (820) is displayed in image (800). In the alternative, guideline (830) may be displayed in image (800), but then deleted when surgical instrument (820) is moved by the user and/or when a portion of surgical instrument (820) is displayed in image (800). In the alternative, guideline (830) may be generated but not displayed. In the alternative, the color or colors of guideline (830) may match the color or colors of the eye so as not to be perceptible to the user.

When guideline (830) and one or more surgical instruments (820) are displayed simultaneously in image (800), guideline (830) may be displayed as "above" (i.e., in front of) surgical instrument (820) so it is visible regardless of the position of surgical instrument (820). In the alternative, guideline (830) may be displayed "below" (i.e., in back of) surgical instrument (820) so that a portion of guideline (830) is not shown when surgical instrument (820) is positioned over surgical instrument (820). In the alternative, the color, weight, and/or other characteristic of all, a portion, or portions of guideline (830) may be altered as surgical instrument (820) passes "above" guideline (830). For example, if guideline (830) is a solid, black line, when surgical instrument (820) passes above guideline (830), the portion of guideline (830) covered by surgical instrument (820) may be changed to a dashed line and/or may change to the color gray.

As the trainee uses the displayed tool (820) to make a virtual incision, image (800) may display an incision line (840) indicating the path of the incision. Incision line (840) may be black, white, or a color. The color of incision line (840) may be the same color as, or a different color than guideline (830), if guideline (830) is shown. Incision line (840) may be shown as the incision is made, may be shown immediately after the incision is completed, or may be shown at a later time, including during review of the assignment with a trainer.

If incision line (840) deviates beyond a predetermined acceptable distance from guideline (830), at the time the incision is made or after the incision is completed, the system may provide feedback to the trainee that the incision is not sufficiently similar to guideline (830). The deviation may be measured, for example, by the distance between the incision line (840) where the surgical instrument (820) is making an incision at a particular time and the nearest point on the guideline (830). Different acceptable deviations may also be set for each side of guideline (830). For example, the acceptable deviation may be up to one centimeter on one side of guideline (830), but may be only three millimeters on the other side of guideline (830).

Feedback to indicate to the user that the deviation is beyond an acceptable distance may include, for example, vibration in one or more tool handles, a haptic force on a tool handle in the direction that the tool would need to be moved to reduce the deviation, an audible sound, and/or a visual indication on the display. The system may also simulate a noise uttered by the simulated patient if the deviation exceeds a certain threshold.

Also, as shown in FIG. 8, one or more gauges may be shown in image (800). The one or more gauges may provide information concerning the performance of the procedure and/or a simulated condition of the eye. For example, gauge (850) may indicate intraocular pressure (IOP) of the eye, and may show the changes in intraocular pressure as the simulated surgery progresses. If the trainee causes a tool to press against the eye (810), gauge (850) may indicate an increase in intraocular pressure. The one or more gauges may be shown over the eye and/or adjacent to (below, above, or beside) the eye.

Figure 9:
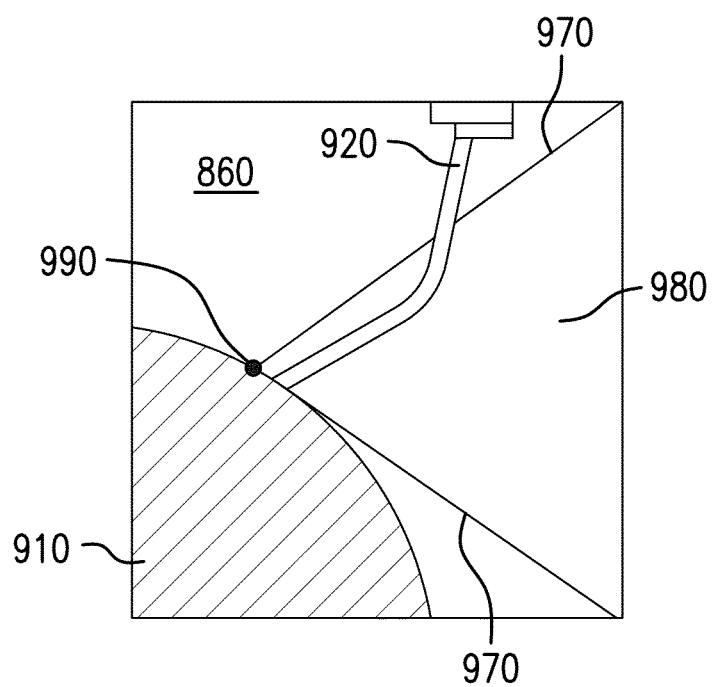
FIG. 9 depicts a simulator user interface in accordance with the present invention.

Also as shown in FIGS. 8 and 9, a two-dimensional view (860) showing surgical instrument (920) and eye (910) may be provided in image (800). Two-dimensional view (860) may be displayed in a window, and/or it may be shown over eye (810) (as shown in FIG. 8) or adjacent to eye (810). Two-dimensional view (860) may show the angle of surgical instrument (920) in relation to eye (910), and the relative distance between the tip of surgical instrument (920) and eye (910). Two-dimensional view (860) may help the trainee gauge the orientation of surgical instrument (820, 920) with respect to eye (910), and the spatial relationship between surgical instrument (820, 920) and eye (910).

The angle of surgical instrument (920) may be measured, for example, as the angle between the line tangential to the closest point of the surface of eye (910) to the tip of surgical instrument (920), and the angle of the closest portion of the surgical instrument (920) to the eye (910). In addition or in the alternative, the angle of surgical instrument (920) may be measured with respect to a reference plain generated by the system.

Two-dimensional view (860) may show a range of preferred or required angles for surgical instrument (820, 920). As shown in FIG. 9, a range of preferred or required angles may be shown by one or more range lines (970). Range lines (970) may be any type of line, including solid, dotted, or dashed. Area (980) of two-dimensional view (860) between range lines (970) and/or the area of two-dimensional view (860) outside the range lines (970) may be highlighted with a color.

A highlight color in area (980) and/or outside the range lines may be applied or changed depending on whether the angle of surgical instrument (820, 920) is within a preferred range. For example, if the angle of surgical instrument (820, 920) is between range lines (970), area (980) may be highlighted with the color green. If the angle of surgical instrument (820, 920) deviates from the preferred range, area (980) and/or the area outside the range lines (970) may be highlighted in a different color (e.g., red), providing an indication to the trainee that the angle of surgical instrument (820, 920) should be adjusted to within the preferred range. In the alternative, the entire two-dimensional view (860) or another sub-portion of two-dimensional view (860) may be highlighted in a color (e.g. red) if the angle of surgical instrument (820, 920) extends beyond a preferred angle or range of angles.

Two-dimensional view (860) may also include an indication (990) on the outer surface of eye (910) showing a preferred or required location where surgical instrument (820, 920) should contact the eye (e.g., where an incision should be made). The system may measure the number of times that surgical instrument (820, 920) is brought within a predetermined distance of eye (810, 910) and/or indication (990) before surgical instrument (820, 920) makes contact with eye (810, 910). The system may require that number of times to be below a predetermined value to constitute a successful procedure. For example, if the trainee causes the tip of a virtual scalpel to approach within two centimeters of the surface of eye (810, 910) more than three times before beginning an incision, the system may indicate that the trainee has not passed the assignment.

Although the examples described above refer to MSIC surgery, the system according to the present invention may be used to train a user to perform any type of surgery. The system may also be used to quickly test whether surgeons or other physicians have the manual dexterity and spatial or depth perception required to perform a surgical procedure, immediately before the procedure is performed or any time before the procedure. For example, an elderly surgeon may not recognize that their manual dexterity has deteriorated or that a decrease in their eyesight has impaired their depth perception until after they have begun the procedure, or until after they fail the procedure. A system in accordance with the present invention could quickly test physicians to determine whether they should not perform a procedure at a particular time. For example, a physician scheduled to perform an MSICS may perform a simulated MSICS, a simulated subset of the steps required to perform an MSICS, or one or more other simulated exercises that can gauge the physician's performance. For example, the physician may be required to guide a simulated scalpel at a particular angle (or at an angle within a given range of angles) and to a particular location on the surface of a simulated patient. The physician may only be allowed a set number of tries to bring the scalpel within a predetermined distance of the patient surface at that location and angle to pass the test. A similar test may be used by medical students considering whether to specialize in medical fields that require a high degree of dexterity before they decide in which field they intend to practice. A similar test may also be used for persons in other fields. For example, the system may be used to test persons intending to operate industrial cranes.

Software and Computer Components

Figure 3B:
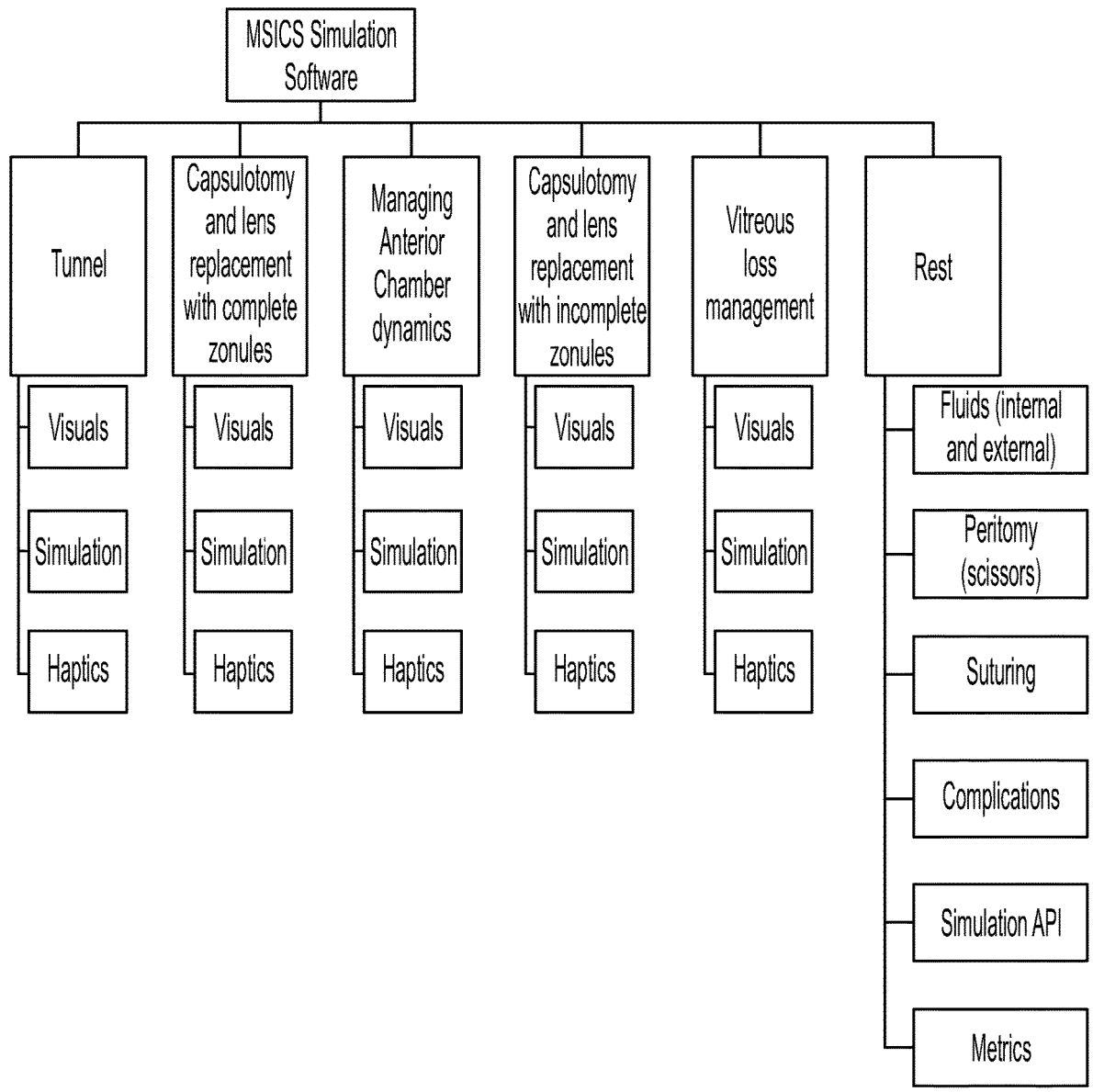
FIG. 3b is a chart illustrating software components of a simulator in accordance with the present invention.

FIG. 3*b* illustrates software components of the simulator, including components for simulating (1) the tunnel, (2) capsulotomy and lens replacement with complete zonules, (3) managing anterior chamber dynamics, (4) capsulotomy and lens replacement with incomplete zonules, and (5) vitreous loss management. Each of those components has a visual, simulation, and haptics subcomponent.

The simulator software is programmed to support performance of the entire MSICS procedure on the MSICS simulator. The software is built around physics based models of the eye, the surgical instruments and the forces experienced during live surgery. Particularly, the software contains the graphic eye models, haptic models, and the courseware/user interface. The haptic and visual responses to interaction with the model are nearly indistinguishable from real surgery. This model reproduces precise tool-tissue contact, realistic tissue resistance, stiffness, flexibility and texture providing realistic feeling of handling the instruments with the simulator hand pieces. The simulator provides sufficient degrees of freedom for movement to allow proper simulation and force feedback.

Figure 3C:
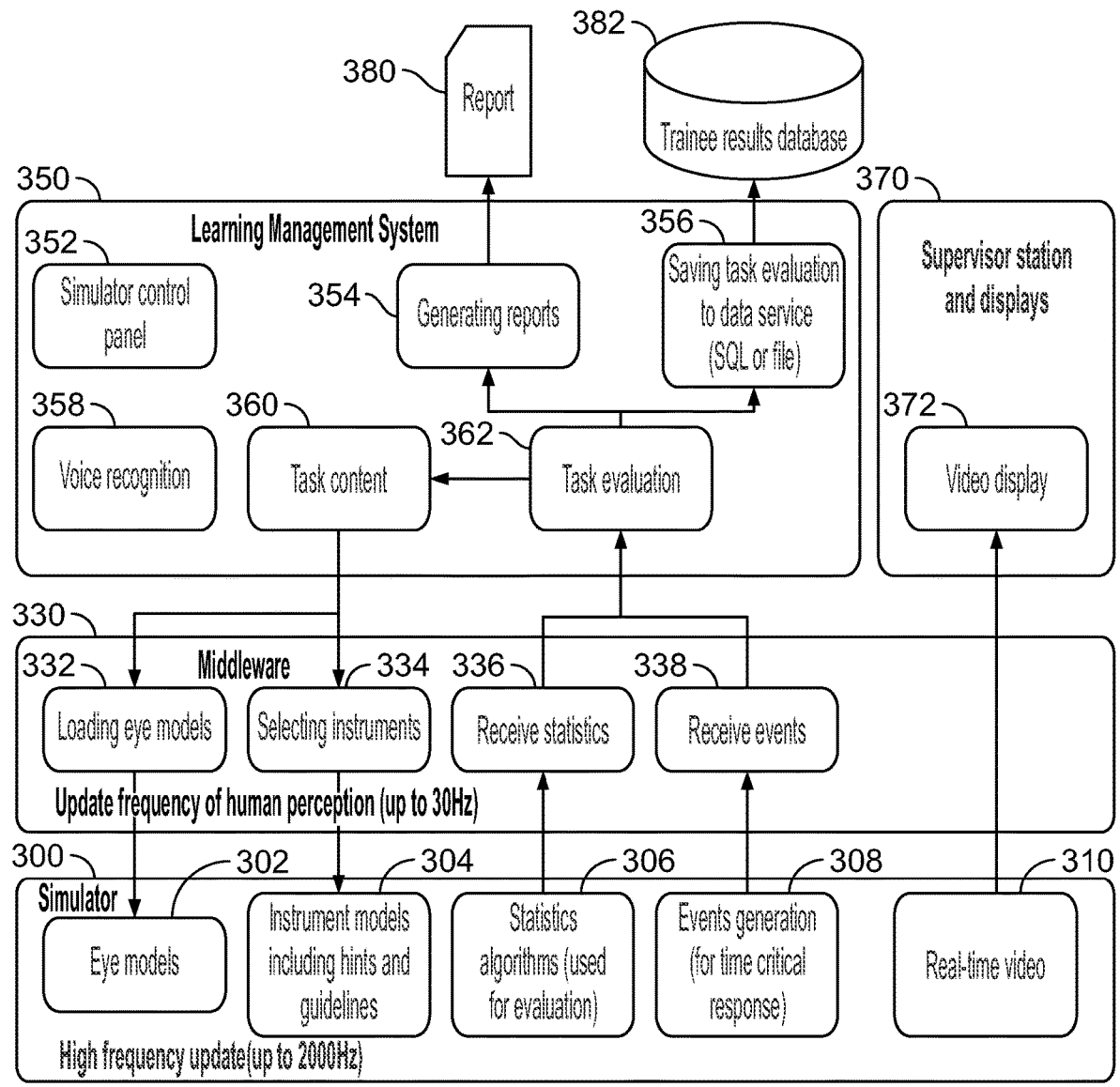
FIG. 3c is a chart illustrating computer components of a simulator in accordance with the present invention.

As used herein, the term "computer" may refer to a stand-alone computer which may include one or more processors and may include memory, or the term "computer" may refer to one or more computer processors. As shown in FIG. 3c, the simulator consists of a plurality of computers, including the Simulator computer, the Courseware or "Simulator Interface Application" (SIA) computer, and the Application Programming Interface (API). A simulator computer, or "graphics and/or real time PC", hosts and runs the simulator software (3-D eye and physics model) and related code. The Simulator computer (300) includes components for eye models (302), instrument models including hints and guidelines (304), statistics algorithms used for evaluations (306), events generation for time critical response (308), and real-time video (310).

A Courseware (Panel PC) computer (350) runs the "Simulator Interface Application" (SIA). The Courseware computer (350) may include components for a simulator control panel (352), generating reports (354, 380), saving task evaluation to data service (356), voice recognition (358), task content (360), and task evaluation (362). Trainee results may be saved to a trainee results database (382). The supervisor station (370) includes a video display (372). The principal function of the SIA is to communicate with the simulator in order to deliver training. The SIA allows monitoring, interacting with, and managing the particular student that is currently practicing on the simulator as well as record that student's performance data. To accomplish this, the SIA interacts with the Simulator Based Learning System (SBLS), as described below, to enable the student to view active Assignments (allowed based on prerequisite conditions), and to download specific Assignment files and content/learning resources corresponding to the Assignment selected by the student. Upon completion of the Assignment performance, the SIA uploads the student's performance data at the end of each attempt and the session. When the student reaches proficiency criteria on an Assignment, the list of active Assignments are updated. The SIA may comprise similar modules described below with respect to the SBLS, including: Assignment Database, Learning Experience Logic, Assignment Information Screens, Simulator Communication, Performance Records, SBLS Interface, Video encoding, streaming, and storage, Reports, and Data/Code Update. The Simulator Communication module allows the SIA to communicate with the Simulator using the Simulator API to manage Assignment performance. Such communication is based on the standard Assignments that are received from the SBLS, as described below. In order to track each Assignment performance, trainees authenticate access in order to identify them and store their performance data to their respective records.

A Simulation Application Programming Interface (API) (Middleware layer) interfaces the simulator computer with the SIA. The Middleware layer (330) may include components for loading eye models (332), selecting instruments (334), receiving statistics (336), and receiving events (338). API can be hosted and run either on the graphics PC or Panel PC. An interface is provided for Ethernet communication between the courseware and simulator in order to start simulations, trigger events, getting metrics and other communication that is necessary. The communication requirements between SIA and Simulator Middleware include: Assignment parameters—Eye model configuration and state, Performance Data—Event based, Performance Data—General (Ongoing), Event triggers, Audio Commands, Video Feed, Calibration and Pre-session checks, Performance Logs, and Guidelines, Orientation view and Real time feedback. The major elements of communication between SIA and simulator include:

1. Surgical Conditions:
   a. Surgical Starting Point (a stage within the MSICS surgical procedure).
   b. Surgical Ending Point (a stage within the MSICS surgical procedure).
   c. Common Anatomical Variations (e.g. Color of iris, color of skin, anterior chamber depth etc.).
   d. Surgical Variations (right/left eye, intraocular pressure, type of cataract).
   e. Select intraoperative challenges (Pupil constricts during capsulotomy or IOP increase following removal of nucleus).
2. Training Conditions.
   a. Specific Learning Objective(s) for the assignment (e.g. making the scleral groove having required shape and size).
   b. Performance parameters and metrics (e.g. Size of incision, parameters relating to shape of incision).
   c. Standards for evaluation corresponding to metrics (e.g. Range, not exceeding or lower than, event (Yes/No) etc.).
   d. Scoring logic—Points and/or weights and condition relating to each metric to calculate score(s).
   e. Selected training tools—guidelines/orientation view/ real time feedback alerts/aural cues (setting to communicate if these training tools will be made available or not during performance).
3. Assignment Performance Data:
   a. Receive data on assignment performance parameters, metrics, alerts, triggers etc.
   b. Receive video feed.
4. Commands:
   a. Start assignment (transfer and loading of assignment files).
   b. End/Abort Assignment (mark end of performance and ask to initiate performance data transfer).
   c. Verbal commands—for limited purpose (e.g. ask for instruments (to be loaded etc.).
   d. Trigger certain intraoperative challenges (e.g. Microscope bulb failure, patient complains of pain etc.).

The above is not an exhaustive description but fairly comprehensive view. There may be some limited additional communication requirements.

To deliver the training in the most effective manner, the SIA contains the following important features. It breaks down the procedure into smaller segments for unit practice. This allows repeated practice with segments to help focus on specific tasks or task groups. For example, assuming that the procedure is broken down into 10 tasks, one should be able to start with task 5 and stop after completing task 6. When starting at task 5, all the actions from task 1 to 4 would have already been completed and such updated state of the eye should be loaded for performance. The SIA also collects data on performance metrics (data generated on the simulator relating to the performance activity) to compare them with standards and therefore provide both formative and summative feedback. Formative feedback help improve learning. For instance, force being applied for a task was more than required resulting in poor performance or an incision made of a size much bigger than what was required. And summative feedback means assessment of performance in line with the goals. Summative feedback also involves evaluation of performance across attempts. The SIA configures scenarios same as in real life to prepare trainees suitably in managing them effectively. These could be scenarios would include intraoperative challenges such as excessive bleeding in response to an action, weak zonules that hold the capsule, and other challenges that are presented even as the task is performed accurately. Errors or suboptimal performance in earlier tasks can also lead to intraoperative challenges later in the surgery. In order to present such scenarios, without requiring a learner/trainer to create them every time they need to be practiced, the SIA saves the state of the eye such that the trainee can start practicing with that state.

Figure 3D:
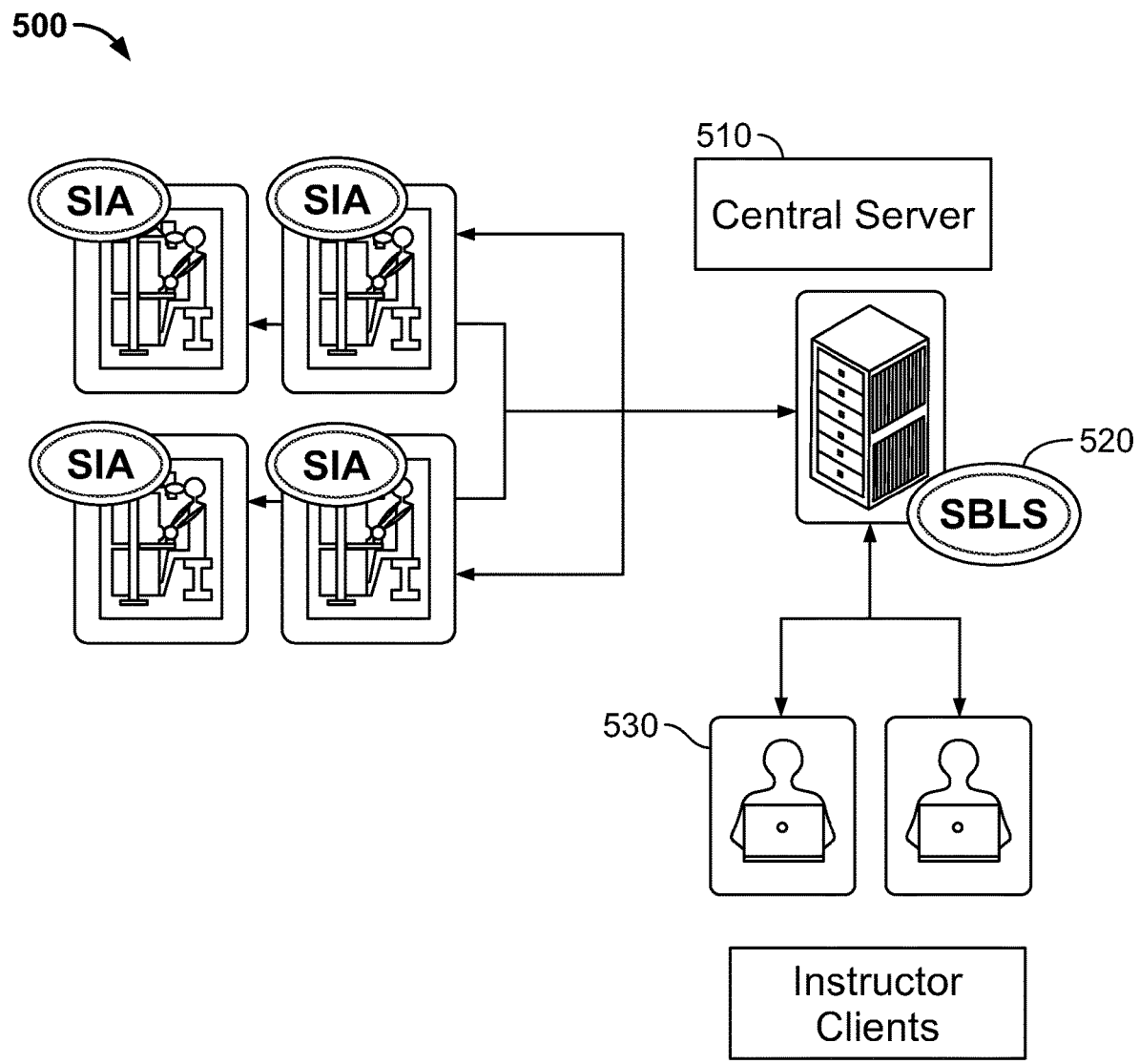
FIG. 3d is a chart illustrating an exemplary connection between a simulator, a central server and instructor clients in accordance with the present invention.

As shown in FIG. 3d, SIA (500) is part of the simulator and manages communication and data exchange with MSICS simulator for each learner and each assignment and their performance of the simulator assignments. In a preferred embodiment, the simulator is connected via an intranet to a central server (510). A server or network application, called the Simulator Based Learning System (SBLS) (520), is hosted on the central server (510) and is used to manage training delivery to a plurality of trainees. SBLS (520) manages learning management across all modes of instructional delivery simulators. It involves management of multiple learners, simulators, training delivery methods, etc. For example, the SBLS (520) may manage more than 50-100 simulators. When the simulators are operating simultaneously, a large amount of rich data in the form of video feed, etc. will be generated and exchanged between the simulators and the centralized server application (SBLS (520)). The SIA (500) communicates with the Simulation API (FIG. 3c) in order to manage simulation practice units i.e. assignments and exchange necessary information. The SBLS (520) manages delivery of the assignments for each trainee, identifies trainees, controls access to assignments, record performance data from assignment attempts, and provides other such training management features. The communication between SIA (500) and SBLS (520) includes: interface for enabling user authentication, sync up with SBLS (520) to maintain local copy of Assignment database (static files and codes relating to assignment evaluation and scoring), transfer performance data, video, etc. to SBLS (520) for updating trainee records on the SBLS (520), and instructor functionalities related communication.

SBLS (520) may comprise a plurality of modules, including the modules listed below. Preferably, a copy of selected modules or certain code from the SBLS (520) is maintained on the SIA (500). This ensures that the simulator practice can be started or continued without any dependence on the SBLS (520). As such, the SIA (500) may comprise the same modules listed below as the SBLS (520). The SIA (500) communicates with the SBLS (520) for data such as the following: user authentication, trainee status information (past records, allowable Assignments), content access relating to Assignments), data Sync with SBLS (520) (upload performance data of trainees that is stored on local system to the SBLS (520) on the network), communication with instructor client (530), transfer of video feeds, download and update latest version of SIA (500), and upload reports and issues from simulator calibration and tests.

Instructor/Student Operation

A module may be used for managing various users (e.g., super user, administrator, instructor (trainer), trainee) and providing access control functionality. The same or a different module may be used to create assignments that can be assigned to the learners for practice and evaluation on the simulator. A trainee will be guided to undertake practice of a set of "Assignments" that will be designed to provide sufficient practice to the trainee on various segments of the procedure and then the entire procedure. The complexity and difficulty levels of each such assignment will increase with progress made by the trainee. The trainees are exposed to wide variety of cataract cases and complications using the assignments. The assignments are created based on selections of several conditions, training tools, performance parameters, triggers/alerts, scoring, pre-requisites, assignment meta-data etc.

Each practice unit on the MSICS simulator is referred to herein as an Assignment. Each Assignment may have a starting and an ending point (within the MSICS procedure), each indicating the state of the eye and related parameters (e.g. color, size, type of cataract etc.). An Assignment may be a segment of a procedure wherein some tasks would have been already completed (e.g. eye with scleral groove has been made). An Assignment may also include complications to be presented. The SBLS may support a database of a large number of MSICS surgical Assignments using a user-friendly interface and a series of steps to capture and set all the data to define a typical assignment.

Each Assignment may include all of the information required by the simulator to: (1) begin the simulation (using selections possible for surgical conditions, training conditions, i.e. appropriate eye model variables, patient parameters, standard/custom starting point in the surgical procedure; (2) define access to training tools—provision of guidelines, orientation view and feedback (real-time); apply other level wise settings and tolerances for errors and alerts etc., possible complications and corresponding action; (3) determine the end of the simulation based on trigger of certain conditions viz. vision threatening complications in specific assignments (level 2), abortion of Assignment by trainee, completion of Assignment performance, instructor intervention etc; (4) allow communication of alerts and performance metrics—in real-time and end of Assignment (facilitates feedback relating to errors, computation of score for the attempt, provision of detailed breakdown of scores awarded for each parameter etc.); (5) intervention by instructors to alter/trigger certain modifiable conditions; and/or (6) validation of instruments to be used with each part of the simulation Assignment. Each Assignment may also include reference data corresponding to each performance parameter specified to enable evaluation. Corresponding to each level there may be a specified value, range or setting against which the parameters will be compared to assign a score or pass/fail status.

An assignment database may store assignments and corresponding data that may be communicated to the simulator using, for example, XML messages/commands. The Assignment files may include one or more of the following details: (1) associated performance metrics expected to be monitored and/or recorded in real-time and after the Assignment attempt has been completed; (2) Guidelines, Orientation view and Real time feedback requirements (includes Aural feedback and other aural requirements); (3) scenarios for complications that can be triggered by the instructor; (4) triggers for events; (5) parameters (metrics) linked to feedback remedial content resources; (6) reference starting point name and data files corresponding to a custom starting point (saved following a trainee or trainer performance); (7) Assignment Meta data: Task Group/Task/Subtask/Movement Number according to standard proficiency definition for MSICS, Title, description, tags—level, task group etc.

A Simulator Validation Study may include, for example, a set of 30-40 Assignments, having about 8-10 unique Assignments, each with 2-3 small variations. In such variations, base assignment files can be leveraged for customization in terms of metrics to be used for scoring and alerts and triggers may change to emphasize certain specific learning objective(s) relating to the Assignment. For instance, an Assignment relating to "making the scleral groove" might have as one of its variants an emphasis on the trainee getting the shape of the groove correct and its metrics may have higher weightage when scoring. Other metrics collected, such as length of the groove, depth of the groove etc., may carry low or no weightage. Therefore, the weightage applied to each metric for the score may vary accordingly for providing suitable emphasis corresponding to the learning objective(s).

Assignment Information Screens may include a set of screens that provide information for each Assignment, including graphics, videos, animations etc. The screen can have links that can load further details in pop-up screens. These screens will present standard information on the assignment such as Assignment Description, Steps to Perform, Surgeon Cues, and Best practice to follow, video of expert performance, video from actual surgery etc.

Learning Experience Logic may evaluate each unique Assignment, determines completion of Assignment based on proficiency requirements, determine the flow or order in which Assignments will be made accessible to users, etc. The trainee's experience on the simulator may be determined by a number of features. One of the important ones amongst them may be "individualization." One of the features relating to individualization may be managing a trainee's progress through a list of assignments. This can be computer controlled or controlled by a trainer.

A trainee may be expected to progress through the Assignments in a definite order in the computer controlled mode. While it may be possible for the trainee to view the list of Assignments, only those that he or she is qualified to access as per this predefined order may be displayed as active Assignments. "Active" Assignments mean those assignments that are enabled for practice. "Inactive" Assignments may become "Active" when pre-requisite Assignments are completed by the trainee. The trainer can give each trainee access to any assignment (in any order) or enable/disable access to each assignment based on his individual judgment. In addition, trainers may be allowed to change select conditions (specifications provided within the Assignment) referred to as modifiable conditions. Modifiable conditions refer to a selection of conditions for the surgical simulation that any trainer can change to enhance the training experience.

An Open Assignment is available to the trainer in trainer control mode. It may be configured with default simulation conditions. Default conditions are the most basic settings for simulator practice. The trainer may be able to make changes using modifiable conditions (e.g., within these default conditions and some others) and surgical start point before allowing the trainee to begin the open assignment attempt. The purpose of the open assignment may be to allow trainee familiarization with the simulator setting and the assignment conditions before initiating formative or summative evaluation of the attempts. Standard parameters and performance video may be recorded for each attempt. However, attempts to this assignment may not be evaluated and scored by the system. The trainer can enter attempt feedback notes into the system.

A computer control mode may also be provided where preset algorithms govern the access to assignments in the assignments library and progression across assignments. However, a trainer may have the ability to override the setting for a trainee, for select assignments and to permit access. In this mode, the trainees can continue practicing assignments without requiring instructors to closely monitor and determine access. However, instructors may be required to review the performance data and provide feedback either on a real time basis or later for the attempts.

A Free Play feature within computer control mode may allow for a predefined number of attempts corresponding to each assignment as Free Play. The purpose of Free Play mode may be to allow a trainee familiarization with the simulator setting and the assignment conditions before initiating formative or summative evaluation of the attempts. However, performance data may still be recorded for monitoring of simulator use.

Each Assignment may need both formative and summative evaluation. For evaluation, several parameters may be monitored and stored during and after the Assignment performance. Summative evaluation may require using select metrics and comparing them with set standards of performance to assign a score and/or classify an attempt as a "successful" or "failed" attempt. A composite score may be calculated from these metrics. This may be required to benchmark performances and facilitate comparison with other attempts by the same user (or other users with the use of the same standards). A simplified example to demonstrate this requirement is set forth in the following table:

| Performance Parameter | Parameter A | Parameter B | Parameter C | Composite Score |
|---|---|---|---|---|
| Standard | 5.00 mm | 5.00 mm | 5.00 mm | 80 |
| Actual | 4.70 mm | 4.62 mm | 4.2 mm | 16 |
| Range 1 - Score | 4.70-5.30 (40) | 4.70-5.30 (40) | 4.70-5.30 (40) | |
| Range 2 - Score | 4.40-4.69 or 5.31-5.50 (15) | 4.40-4.69 or 5.31-5.50 (15) | 4.40-4.69 or 5.31-5.50 (15) | |
| Critical Errors | No | Yes | No | |
| Outcome | ✓ | X | X | |
| Actual Performance Score | 40/40 | FAIL | 0/40 | 16 |
| Weight | 40% | 30% | 30% | FAIL |

An Assignment may be considered completed when a desired level of proficiency is demonstrated with consistent performance recorded across a series of attempts. The completion requirement may also mandate certain amount of practice in the form of minimum number of attempts required, minimum number of successful attempts, and minimum number of consecutive successful attempts.

Free play may include a pre-set number of attempts that allowed to each trainee for each assignment before the performance data from attempts is considered for scoring and progression. It may allow them to familiarize themselves and get comfort with the task on hand before they are monitored and evaluated. Such requirement for each Assignment may be set as part of the progression and/or evaluation logic. A sample completion requirement for a typical assignment may include: (1) Minimum Attempts Required (e.g., 80 to ensure sufficient practice); (2) Minimum Successful Attempts (e.g., 40 to ensure certain minimum amount of success); (3) Minimum Consecutive Successful Attempts (e.g. 37 to ensure consistency in successful performance); and/or (4) Free-Play (e.g., 15 to allow familiarization with assignment, without any pressure relating to performance review or evaluation). According to one embodiment, during Free-Play, no score may be assigned and no feedback may be provided. However, performance data may still be recorded for monitoring purposes.

A simplified example of recorded attempts is illustrated in the table below:

Assignment No. 1
Free-Play: 4 Attempts
Min. Successful Attempts: >3
Min. Consecutive Successful Attempts: At least 3
out of last 5 (3/5) attempts must be successful

| Attempt No. | Score | Outcome - (Successful Attempts) \| Consecutive Successful Attempts | Requirement Status |
|---|---|---|---|
| 1 | 16 | Fail (NA) | NA |
| 2 | 40 | Fail (NA) | NA |
| 3 | 55 | Fail (NA) | NA |
| 4 | 81 | Pass (NA) | NA |
| 5 | 64 | Fail (0/5) \| 0 | Continue Practice |
| 6 | 69 | Fail (0/5) \| 0 | Continue Practice |
| 7 | 87 | Pass (1/5) \| 1 | Continue Practice |
| 8 | 75 | Fail (1/5) \| 0 | Continue Practice |
| 9 | 96 | Pass (2/5) \| 1 | Continue Practice |
| 10 | 95 | Pass (3/5) \| 2 | Continue Practice |
| 11 | 97 | Pass (4/5) \| 3 | Completed |

A Performance Records Database may be used to store a log of all learner attempts for each of the Assignments, storage of scores, metrics, videos, etc. Each attempt by a trainee may be recorded and stored. The data generated may be stored on the SIA/SBLS. It may include video recording, time taken for each attempt, performance parameter values, scores, count of attempts (successful, unsuccessful, aborted), count of last consecutive successful attempts, etc. These may be used for reporting, analysis and also may be used within the logic for progression across Assignments as shown above. The SIA may transfer the records/data of Assignment attempt to the SBLS for each trainee immediately after each attempt. Additionally other data such as login time, logout time, time taken for attempts and session length may also be collected and stored for each trainee The system may allow exporting performance data collected, including video recordings. Records of raw 3D model parameters may be stored at predefined stages of the Assignment performance or on demand. Such raw 3D model snapshots can be exported from the SBLS for review and used by a courseware design team. It may be used to set up unique states of the eye model when creating assignments.

An Instructor Module may allow an instructor to monitor and manage simulator practice sessions. The instructor can connect with the SBLS using a desktop/laptop PC and preferably a tablet. The instructor module may have the following functionalities for accessing the SBLS and managing the delivery of training: (1) View a dashboard of simulator lab activity—simulators and current user activity; (2) Monitor Assignment performance using video data stream, where the trainer can view a set of video streams together, or select one and toggle between views; (3) Get real time and event based updates/messages; (4) View reports; (5) Add subjective comments to each Assignment attempted by a trainee; (6) Add or reduce scores for an Assignment attempt based on subjective evaluation and observation; (7) Review trainee performance history; and/or (8) Override learning experience logic to allow trainees to progress or prevent progression due to subjective evaluation or other such reasons. An Instructor can also login from the simulator Panel PC to access these features and use it for performing Assignments, just like the trainees.

Reports may be generated and viewed. The presentation of each report may be filtered, changed in views, and sorted and customized. Reports may including:

Assignment Status report by the assignment for a group of trainees.

Individual trainee progress report for each assignment and across all assignments.

Training activity report (for a trainee or group—for a selected period of time/days).

Learning analytics (charts and tables)—for assignments (individual, group and comparison)—some examples are given here:

Trend—successful, failed, aborted attempts.

Average time for successful (other status) or all attempts.

Number of attempts to proficiency.

Trend of performance—for selected metrics within an assignment (one or more metrics selected).

Instructor comments for an assignment.

Number of attempts and time spent on each attempt for each assignment.

Number and sequence of failed attempts during an assignment (failed means assignments ends due to a vision threatening error).

Number of failed attempts by sim level (2 or 3).

Number and sequence of aborted attempts during an assignment.

Number of aborted attempts by level.

Number and sequence of successfully completed attempts during each assignment.

List number and description of vision threatening errors for each assignment by date of attempt.

Report of selected metrics by assignment and date (as per interface requirements metrics list above) after each 10 attempts.

Simulation software, which may include the core simulation and the simulator API code, may be updated periodically to, for example, fix issues and upgrade the functionality. In addition, to enable use of simulators independent of SBLS, certain code and data may be maintained locally on the SIA. This may include data such as Assignment Library and code such as logic for progressing through assignments etc. In case there are updates, the data/code update module may be allowed to push these to each of the simulators either periodically or on demand. A check may be run periodically to confirm the latest version installed, and update simulators as may be required.

The following table provides a Use Case Scenario that connects various activities with the functions of the simulator and associated components and features, including the Simulator Based Learning System (SBLS):

| Typical progression of training activity on the simulator |
|---|
| Turn On the simulator: It turns on the Panel PC that runs the Simulator Interface Application (SIA) automatically on startup. |
| Login Screen displayed on adjunct screen. |
| Trainee logs in with ID and Password/Code. Instructor can also login using the same screen. |
| A list of assignments is displayed on adjunct screen. The list will also be present if the assignment is active. That is, enabled for beginning or continuing practice. |
| The simulator can restrict access to assignments for managing the order in which they must be practiced. However, the instructor will always have unrestricted access to launch any Assignment, at any time. This data is loaded from the SBLS. |
| Trainee/Instructor select the assignment to begin practice. |
| The instructor can disable the restriction on access and change all the assignments to be active. |
| The Assignment description screen will be displayed with a "Begin" button. |
| The description content includes text supported by media elements such as images, videos and animations that can be viewed by the user. The content can be layered (one-level) - links made available to load pop up screens. |
| Trainee begins performance by touching the "Begin" button on screen. |
| A record of the Assignment attempt is created on the SBLS. On completion of the attempt, it will be updated with the corresponding data received from the SIA. |
| An instructor can login to the network application (SBLS) at any time to view a dashboard which lists all the simulators on the network, ongoing trainee activity, their status etc. |
| The SIA communicates to the Simulator via the Simulator API - Selected Assignment related files transferred to the simulator. The assignment files define starting point, ending point from the surgical procedure to be practiced, eye model configuration/settings, list of parameters to be tracked real-time and metrics to be provided at the end of performance. Alternatively, these files are received from SBLS on selection and passed on to the Simulation API. |
| The simulator uses the assignment files to load the eye model and the simulation activity can begin. The trainee picks up the instrument handles (haptic arms) and looks through the microscope to begin. |
| Trainee gives verbal commands asking for instruments - left and right hand. SIA has voice recognition capability for several verbal commands - these trigger sending commands (using XML files) to simulator for corresponding action. |
| Simulator gives audio alert in case incorrect instrument is selected. |
| Trainee brings the instruments in the field of view (microscope viewer) and begins the performance. |
| Real time parameters required by SIA are monitored and alerts provided in case alert conditions are met. All other metrics required are recorded during the assignment attempt. |
| Guidelines, Orientation view and Real time feedback are made available (as per the Assignment settings). Guidelines and Orientation view are artificial objects (lines, arrows etc.) displayed in microscope view for trainee performance support. Feedback is audio alert on trainee errors and short text message appearing with it for a few seconds to communicate the nature of error. These can be turned On/Off by a verbal command. |
| Any specific error or condition that is classified as "complication" may result in halting of the performance as per the assignment settings. The simulator will display a message communicating the event to the trainee. These conditions are preset in the simulator software. An alert to keep this condition active for monitoring is set or registered when Assignment files are transferred to the simulator. |
| The instructor client will also be able to view the alerts for which triggers have been configured as part of the Assignment specifications. |
| The instructor/trainee can switch between real-time video on the adjunct screen OR keep the Panel PC - SIA interface displayed. Essentially, the adjunct display can be used for connecting to one of the two display feeds: 1. Panel PC - SIA application interface or 2. HDMI video feed directly from the simulator visual display. |
| The HDMI video feed is also transferred to SIA via the Simulation API and it will be encoded and stored as part of the Assignment attempt data. |
| The instructor client will allow viewing the video stream from the simulator(s) via the SBLS - limited set of simulator videos simultaneously. |
| The trainee or instructor (standing by) can give a verbal command or use an on-screen button to abort or indicate completion of practice unit. |
| End of Assignment performance metrics are communicated to the SIA. |
| SIA receives the performance metrics and calculates scores corresponding to preset rubric for each Assignment. Or transfers the metrics to SBLS for calculations. |
| SIA/SBLS computes a composite performance score. SIA/SBLS provides a success/fail outcome to the performance based on the evaluation rubric. |
| SIA/SBLS updates the Assignment status using a preconfigured proficiency requirement. (Not Started, In progress or Completed). |
| Each assignment may have different completion requirement in terms of performance scores across attempts, or trend of continuous successful performances (i.e., at least 10 successful attempts from last 15 attempts) |
| The assignment performance report is displayed on the screen for the trainee and instructor to review. Reports are represented visually. Some visual representations may be made available through links (pop-up). This will allow the instructor to use the performance data along with his/her observations for attempt evaluation and providing feedback to the trainee. |

| Typical progression of training activity on the simulator |
|---|
| Closing the Assignment Attempt report will display a screen that provides summary of the user's performance history for the Assignment. The performance report for each attempt can be viewed by selecting any attempt from the list (a drill down report). |
| More options/features are made available to the users. They can go to "Reports" screen to select and view other available reports. |
| It will be possible to jump to the Assignments list to select another active Assignment to continue practice, or Log off and close the simulator session. |
| Logging off will update the SBLS with corresponding data viz. time. |
| Immediately after the Assignment attempt is completed and anytime thereafter, the instructor can review the attempt data and add (type in) a subjective evaluation comment and/or edit the score on the Assignment. Such comments and changes will be stored with the instructor identity. Two such notes/edits can be made - the second one allowing expert instructor to provide his/her comments and inputs. The trainee can also add comments or notes relating each attempt after completion. |

Verbal commands may be incorporated into the simulator to increase the realism of instrument changes and intraoperative management. A verbal command asking for an instrument change may be given and the instrument visual under the microscope may change accordingly. In case handles are not the same, the trainee may need to manually change the handles that will be designed to feel like the actual instrument that is chosen for use. Voice recognition is also provided as part of the courseware to support the selection of instruments by voice command and other commands by the trainee.

In some scenarios there may be interactions with scrub nurse requiring the surgeon to communicate with other persons. The simulator restricted to what you see in the microscope and what you feel with your hands. Any other interactions or higher level communication will be handled by courseware and the simulator will provide an interface to the courseware to make any changes to the simulated scene based on whatever interaction is performed on a higher level. For example, the simulator may indicate that the microscope bulb has burned out. In this scenario the microscope bulb burns out and the microscope view dims. The response of the surgeon is to ask the nurse to change the microscope bulb, and when this is done the normal light is restored. The sequence between simulator and courseware is as follows: (1) courseware sends command to simulator that the bulb should burn out, (2) simulator responds by making the view appropriately dark, (3) courseware identifies whatever sequence of events that are required for the bulb to be changed, e.g. voice command to tell the nurse to change bulb, (4) courseware sends command to simulator that the bulb should work properly again, and (5) simulator restores the light in the microscope view.

Heart monitor sounds are also provided. Heart rate is connected to events in the simulator and also be settable from courseware side. In addition, patient sounds, requests, and other sounds are incorporated where the courseware can set sounds to be played at certain events or directly.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A system for simulating a surgery, the system comprising:
   a first haptic arm representative of an actual surgical tool;
   a first haptic mechanism in mechanical communication with the first haptic arm, wherein the haptic arm and haptic mechanism are configured to provide real time haptic force feedback to a user of the system during simulation of a surgery;
   a haptic control unit configured to signal to the first haptic mechanism a level of haptic force feedback;
   a first computer in electronic communication with the haptic control unit and comprising a software module having a physics-based model of a portion of the human body and configured to calculate the haptic force feedback to be provided by the first haptic arm and first haptic mechanism, wherein the calculated haptic force feedback corresponds to substantially the same forces exerted on the actual surgical tool when it interacts with the portion of the human body during live surgery; and
   a simulated microscope having a display,
   wherein the display is configured to show, at the same time and while said system is simulating a surgery, a three-dimensional simulated image of the portion of the human body, a three-dimensional image showing a first simulated surgical tool corresponding to the actual surgical tool, a two-dimensional simulated view of the portion of the human body, and a two-dimensional view showing the first simulated surgical tool, based on the current orientation and position of the first haptic arm under the simulated microscope;
   wherein the two-dimensional view of the first simulated surgical tool is displayed in relation to the two-dimensional simulated view of the portion of the human body including relative orientation and/or position of the portion of the surgical tool to the portion of the human body;
   wherein based upon changes in orientation and movements of the haptic arm under the simulated microscope, the display updates in real time the relative position of the three-dimensional simulated image of the portion of the human body, the three-dimensional image showing a first simulated surgical tool, the two-dimensional simulated view of the portion of the human body, and the two-dimensional view showing the first simulated surgical tool;

wherein the calculated haptic force feedback is based on detected interactions between the first simulated surgical tool and the portion of the human body in the display; and wherein the first simulated surgical tool has a tip at one end of the tool.

2. The system of claim 1, wherein the two-dimensional view of the portion of the human body and the two-dimensional view showing the first surgical tool are displayed within a window on the display, and wherein the entire window is displayed over at least a portion of the three-dimensional image of the portion of the human body.

3. The system of claim 1, wherein the tip of the simulated surgical tool comprises a simulated blade.

4. The system of claim 1, wherein the two-dimensional view shows the angle of the first simulated surgical tool in relation to the portion of the human body.

5. The system of claim 4, wherein the angle is measured as the angle between the line tangential to the closest point of the portion of the human body to the tip of the first simulated surgical tool, and the orientation of the tip of the first simulated surgical tool to the portion of the human body.

6. The system of claim 4, wherein the two-dimensional view further shows two range lines indicating a range of angles for the angle of the first simulated surgical tool.

7. The system of claim 6, wherein an area between the two range lines is highlighted with a color.

8. The system of claim 7 wherein the color changes depending on whether an angle of the first simulated surgical tool is within a predetermined range of angles.

9. A system for simulating a surgery, the system comprising:
a first haptic arm representative of an actual surgical tool;
a first haptic mechanism in mechanical communication with the first haptic arm, wherein the haptic arm and haptic mechanism are configured to provide real time haptic force feedback to a user of the system during simulation of a surgery;
a haptic control unit configured to signal to the first haptic mechanism a level of haptic force feedback;
a first computer in electronic communication with the haptic control unit and comprising a software module having a physics-based model of an eye and configured to calculate the haptic force feedback to be provided by the first haptic arm and first haptic mechanism, wherein the calculated haptic force feedback corresponds to substantially the same forces exerted on the actual surgical tool when it interacts with an eye during live surgery; and
a simulated microscope having a display;
wherein the display is configured to show, at the same time, a three-dimensional, simulated graphical model of the eye and a three-dimensional, simulated first surgical tool corresponding to the actual surgical tool based on the current orientation and position of the first haptic arm under the simulated microscope, and a guideline on the three-dimensional, simulated graphical model of the eye indicating a path for an incision;
wherein based upon changes in orientation and movements of the haptic arm under the simulated microscope, the display updates in real time the relative position of the three-dimensional, simulated graphical model of the eye, the three-dimensional, simulated first surgical tool, and the guideline on the three-dimensional, simulated graphical model of the eye indicating a path for an incision;

wherein the calculated haptic force feedback is based on detected interactions between the first simulated surgical tool and the graphical model of the eye in the display; and wherein the first simulated surgical tool has a tip at one end of the tool.

10. The system of claim 9, wherein the guideline is deleted when the first haptic arm is moved.

11. The system of claim 9, wherein the guideline is deleted when the three-dimensional image of the first simulated surgical tool appears on the display.

12. The system of claim 9, wherein the guideline is displayed as above the first simulated surgical tool.

13. The system of claim 9, wherein the guideline is displayed as below the first simulated surgical tool.

14. The system of claim 13, wherein the appearance of a portion of the guideline is altered when the first simulated surgical tool passes above the guideline.

15. The system of claim 9, wherein the microscope is further configured to display an incision line indicating a virtual incision made by the first simulated surgical tool.

16. The system of claim 9, wherein the incision line is shown as the virtual incision is made.

17. The system of claim 15, wherein the display provides an indication if the virtual incision deviates beyond a predetermined distance from the guideline.

18. A system for simulating a surgery, the system comprising:
a first haptic arm representative of an actual surgical tool;
a first haptic mechanism in mechanical communication with the first haptic arm, wherein the haptic arm and haptic mechanism are configured to provide real time haptic force feedback to a user of the system during simulation of a surgery;
a haptic control unit configured to signal to the first haptic mechanism a level of haptic force feedback;
a first computer in electronic communication with the haptic control unit and comprising a software module having a physics-based model of an eye and configured to calculate the haptic force feedback to be provided by the first haptic arm and first haptic mechanism, wherein the calculated haptic force feedback corresponds to substantially the same forces exerted on the actual surgical tool when it interacts with an eye during live surgery; and
a simulated microscope having a display;
wherein the display is configured to show, at the same time, a three-dimensional graphical model of the eye, a three-dimensional image of a first simulated surgical tool corresponding to the actual surgical tool, and an incision line indicating a virtual incision made by the first simulated surgical tool, based on the current orientation and position of the first haptic arm under the simulated microscope;
wherein based upon changes in orientation and movements of the haptic arm under the simulated microscope, the display updates in real time the relative position of the three-dimensional graphical model of the eye, the three-dimensional image of a first simulated surgical tool, and the incision line indicating a virtual incision made by the first simulated surgical tool;

wherein the calculated haptic force feedback is based on detected interactions between the first simulated surgical tool and the model of the eye in the display; and wherein the first computer generates a guideline for incision on the three-dimensional graphical model of the eye but the guideline is not visible on the display;

wherein the first computer provides an indication if the virtual incision deviates beyond a predetermined distance from the guideline; and wherein the first simulated surgical tool has a tip at one end of the tool.

19. The system of claim 18, wherein the incision line is shown as the virtual incision is made.

20. The system of claim 19, wherein the indication is shown on the display.

* * * * *